(12) United States Patent
Crouzet et al.

(10) Patent No.: US 6,977,174 B2
(45) Date of Patent: Dec. 20, 2005

(54) CIRCULAR DNA MOLECULE WITH CONDITIONAL ORIGIN OF REPLICATION, METHOD FOR PREPARING THE SAME AND USE THEREOF IN GENE THERAPY

(75) Inventors: Joël Crouzet, Sceaux (FR); Fabienne Soubrier, Thiais (FR)

(73) Assignee: Centelion, Vitry-sur-Seine (FR)

( * ) Notice: Subject to any disclaimer, the term of this patent is extended or adjusted under 35 U.S.C. 154(b) by 400 days.

(21) Appl. No.: 09/043,193

(22) PCT Filed: Sep. 13, 1996

(86) PCT No.: PCT/FR96/01414

§ 371 (c)(1),
(2), (4) Date: Mar. 13, 1998

(87) PCT Pub. No.: WO97/10343

PCT Pub. Date: Mar. 20, 1997

(65) Prior Publication Data

US 2001/0014476 A1 Aug. 16, 2001

(30) Foreign Application Priority Data

Sep. 15, 1995 (FR) .............................. 95/10825

(51) Int. Cl.[7] .................. C12N 15/64; C12N 15/70; C12N 15/79
(52) U.S. Cl. ................... 435/320.1; 435/69.1; 435/325; 435/455; 536/23.1
(58) Field of Search .................. 435/6, 91.4, 455, 435/471, 320.1, 252.3, 252.33, 325; 536/23.1, 24.2

(56) References Cited

U.S. PATENT DOCUMENTS

| 4,654,307 | A | * | 3/1987 | Morgan | .................. 435/252.33 |
| 4,761,367 | A | | 8/1988 | Edgell et al. | .................. 435/6 |
| 5,434,065 | A | | 7/1995 | Mahan et al. | ............. 435/172.3 |
| 5,510,099 | A | * | 4/1996 | Short et al. | |
| 5,656,481 | A | * | 8/1997 | Baetge et al. | ................ 435/325 |
| 5,693,622 | A | * | 12/1997 | Wolff et al. | .................... 514/44 |
| 5,700,657 | A | * | 12/1997 | Beaudry et al. | ........... 435/69.1 |
| 5,714,323 | A | * | 2/1998 | Ohshima et al. | |
| 5,773,246 | A | * | 6/1998 | Keene et al. | ............... 435/69.1 |
| 5,859,208 | A | * | 1/1999 | Fiddes et al. | ................ 530/399 |
| 5,955,056 | A | * | 9/1999 | Short et al. | |
| 5,985,644 | A | * | 11/1999 | Roseman et al. | |
| 6,254,874 | B1 | * | 7/2001 | Mekalanos et al. | |
| 6,573,100 | B1 | * | 6/2003 | Seeber et al. | |

FOREIGN PATENT DOCUMENTS

| WO | WO 95/30762 | 11/1995 |
| WO | WO 96/01899 | 1/1996 |

OTHER PUBLICATIONS

Koons et al. Characterization of pPvu1, the autonomous plasmid from Proteus vulgaris that carries the genes of the PvuII restriction–modiciation system. Gene, 1995 vol. 157:73–79.*

Pósfai et al. In vivo excision and amplification of large segments of the *Escherichia coli* genome. Nucleic Acids Research, 199 vol. 22:2392–2398.*

Baum et al. Novel Cloning Vectors for *Bacillus thuringiensis*. Applied and Environmental Microbiology, 1990 vol. 56:3420–342.*

(Continued)

*Primary Examiner*—Karen A. Lacourciere
*Assistant Examiner*—Terra C. Gibbs
(74) *Attorney, Agent, or Firm*—Finnegan, Henderson, Farabow, Garrett & Dunner LLP

(57) ABSTRACT

A circular DNA molecule, useful for gene therapy, comprising at least one nucleic acid sequence of interest, characterized in that the region allowing the replication thereof has an origin of replication with a functionality in a host cell that requires the presence of at least one specific protein foreign to said host cell. A method for preparing same, cells incorporating said DNA molecules and uses thereof in gene therapy are also described.

102 Claims, 10 Drawing Sheets

OTHER PUBLICATIONS

Figure 1:
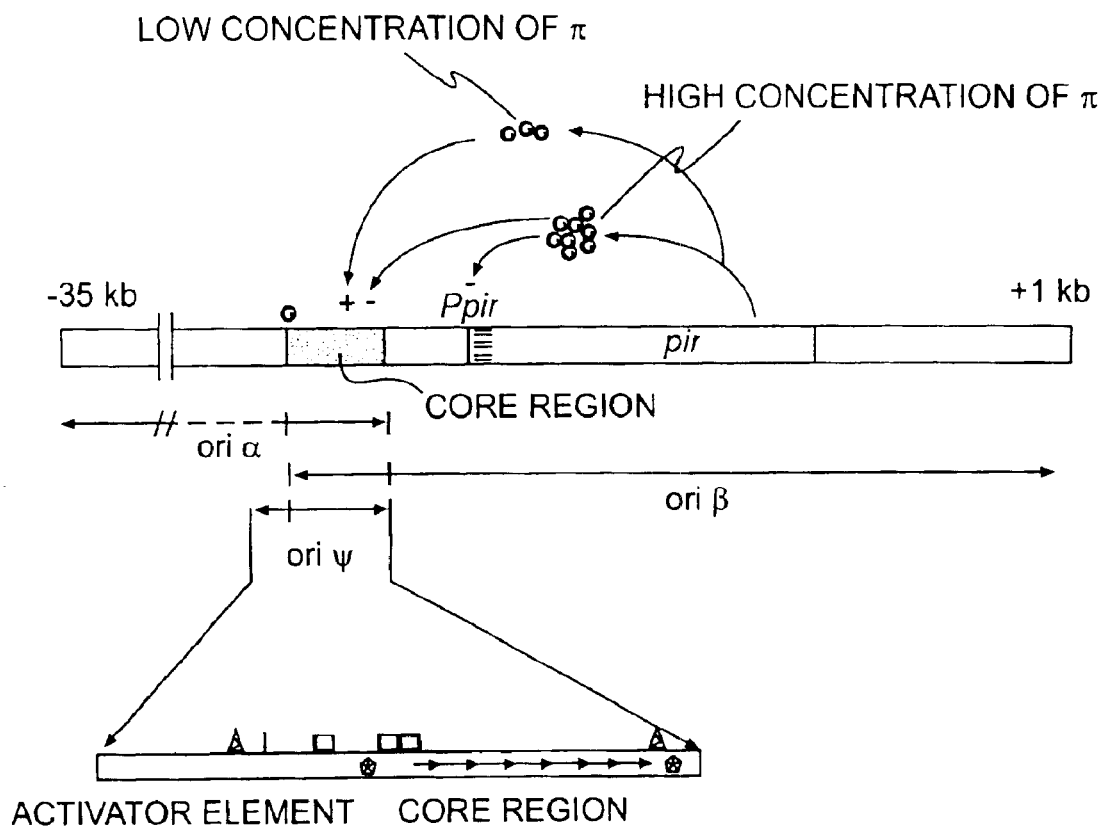

Penfold and Pemberton. An improved suicide vector for construction of chromosomal insertion mutations in bacteria. Gene, 1992 vol. 18:145–146.*

W. French Anderson, Human gene therapy, NATURE, vol. 392, pp. 25–28.*

Winnacker, E.L. *From Genes to Clones*, pp. 132–138, 1987.*

Posfai et al. In vivo excision and amplification of large segments of the *Escherichia coli* genome. Nucleic Acids Res. Jun. 25, 1994;22(12):2392–8.*

Flensburg et al. Bacteriophage P4 DNA replication. Nucleotide sequence of the P4 replication gene and the cis replication region. J Mol Biol. May 20, 1987;195(2):439–45.*

Filutowicz et al. DNA and protein interactions in the regulation of plasmid replication. J Cell Suppl. 1987;7:15–31.*

June Rothman Scott, "Regulation of Plasmid Replication," *Microbiological Reviews*, Mar. 1984, vol. 48, No. 1, p. 1–23.

Dalyot et al., Efficient Transfer Of The Complete Human Beta–Globin Gene Into Human And Mouse Hemopoeitic Cells Via SV40 Pseudovirions. Gene Transfer & Gene Therapy 47–56 (1989).

Rusconi et al., A novel expression assay to study transcriptional activators. Gene 89:211–221 (1990).

Vasavada et al., A contingent replication assay for the detection of protein–protein interactions in animal cells. Proc. Natl. Acad. Sci., USA 88:10686–10690 (1991).

Gluzman. SV40–Transformed Simian Cells Support the Replication of Early SV40 Mutants. Cell. 23: 175–182 (1981).

Herrero et al., Transposon Vectors Containing Non–Antibiotic Resistance Selection Markers for Cloning and Stable Chromosomal Insertion of Foreign Genes in Gram–Negative Bacteria, Journal of Bacteriology, 172(11): 6557–6567 (1990).

Metcalf et al., Use of the rep technique for allele replacement to construct new *Escherichia coli* hosts for maintenance of R6Kγ origin plasmids at different copy numbers. Gene 138: 1–7 (1994).

Summers et al., Multimerization of High Copy Number Plasmids Causes Instability: ColE1 Encodes a Determinant Essential for Plasmid Monomerization and Stability. Cell 36: 1097–1103 (1984).

Inuzuka et al., An initiator protein for plasmid R6K DNA replication Mutations affecting the copy–number control, FEBS Letters 228(1): 7–11 (1988).

Larsen et al., Low–copy–number plasmid–cloning vectors amplifiable by derepression of an inserted foreign promoter. Gene 28: 45–54 (1984).

Bergemann, J., et al., "Excision of specific DNA–sequences from integrated retroviral vectors via site–specific recombination," *Nucleic Acids Research*, 1995, 23(21):4451–4456.

Gage, P. J., et al., "A Cell–Free Recombination System for Site–Specific Integration of Multigenic Shuttle Plasmids into the Herpes Simplex Virus Type 1 Genome," *Journal of Virology*, 1992, 66(9):5509–5515.

Hanzlik, A. J., et al., "A small plasmid for recombination-based screening," *Gene*, 1992, 122:171–174.

Metzger, D., et al., "Conditional site–specific recombination in mammalian cells using a ligand–dependent chimeric Cre recombinase," *Proc. Natl. Acad. Sci. USA*, 1995, 92:6991–6995.

Stewart, G. D., et al., "Plasmids for recombination–based screening," *Gene*, 1991, 106:97–101.

* cited by examiner

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 389 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
TGTCAGCCGT TAAGTGTTCC TGTGTCACTG AAAATTGCTT TGAGAGGCTC TAAGGGCTTC      60

TCAGTGCGTT ACATCCCTGG CTTGTTGTCC ACAACCGTTA AACCTTAAAA GCTTTAAAAG     120

CCTTATATAT TCTTTTTTTT CTTATAAAAC TTAAAACCTT AGAGGCTATT TAAGTTGCTG     180

ATTTATATTA ATTTTATTGT TCAAACATGA GAGCTTAGTA CGTGAAACAT GAGAGCTTAG     240

TACGTTAGCC ATGAGAGCTT AGTACGTTAG CCATGAGGGT TTAGTTCGTT AAACATGAGA     300

GCTTAGTACG TTAAACATGA GAGCTTAGTA CGTGAAACAT GAGAGCTTAG TACGTACTAT     360

CAACAGGTTG AACTGCTGAT CTTCAGATC                                      389
```

(2) INFORMATION FOR SEQ ID NO:2:

(i) SEQUENCE CHARACTERISTICS:
      (A) LENGTH: 960 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

```
TATACAGAAT GATGAGGTTT TTTTATGAGA CTCAAGGTCA TGATGGACGT GAACAAAAAA      60

ACGAAAATTC GCCACCGAAA CGAGCTAAAT CACACCCTGG CTCAACTTCC TTTGCCCGCA     120

AAGCGAGTGA TGTATATGGC GCTTGCTCCC ATTGATAGCA AAGAACCTCT TGAACGAGGG     180

CGAGTTTTCA AAATTAGGGC TGAAGACCTT GCAGCGCTCG CCAAAATCAC CCCATCGCTT     240

GCTTATCGAC AATTAAAAGA GGGTGGTAAA TTACTTGGTG CCAGCAAAAT TTCGCTAAGA     300

GGGGATGATA TCATTGCTTT AGCTAAAGAG CTTAACCTGC CCTTTACTGC TAAAAACTCC     360

CCTGAAGAGT TAGATCTTAA CATTATTGAG TGGATAGCTT ATTCAAATGA TGAAGGATAC     420

TTGTCTTTAA AATTCACCAG AACCATAGAA CCATATATCT CTAGCCTTAT TGGGAAAAAA     480

AATAAATTCA CAACGCAATT GTTAACGGCA AGCTTACGCT TAAGTAGCCA GTATTCATCT     540

TCTCTTTATC AACTTATCAG GAAGCATTAC TCTAATTTTA AGAAGAAAAA TTATTTTATT     600

ATTTCCGTTG ATGAGTTAAA GGAAGAGTTA ACAGCTTATA CTTTTGATAA AGATGGAAAT     660

ATTGAGTACA AATACCCTGA CTTTCCTATT TTTAAAAGGG ATGTGTTAAA TAAAGCCATT     720

GCTGAAATTA AAAGAAAAC AGAAATATCG TTTGTTGGCT TCACTGTTCA TGAAAAAGAA      780

GGAAGAAAAA TTAGTAAGCT GAAGTTCGAA TTTGTCGTTG ATGAAGATGA ATTTTCTGGC     840

GATAAAGATG ATGAAGCTTT TTTTATGAAT TTATCTGAAG CTGATGCAGC TTTTCTCAAG     900

GTATTTAATG AAACCGTACC TCCCAAAAAA GCTAAGGGGT GATATATGGC TAAAATTTAC     960
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GACCAGTATT ATTATCTTAA TGAG                                             24
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GTATTTAATG AAACCGTACC TCCC                                             24
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
CTCTTTTAAT TGTCGATAAG CAAG                                             24
```

-continued (2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GCGACGTCAC CGAGGCTGTA GCCG                24

CIRCULAR DNA MOLECULE WITH CONDITIONAL ORIGIN OF REPLICATION, METHOD FOR PREPARING THE SAME AND USE THEREOF IN GENE THERAPY

The present invention relates to a novel conditional replication DNA molecule which can be used in gene therapy or for the production of recombinant proteins.

Gene therapy consists in correcting a deficiency or an anomaly by introducing genetic information into the affected organ or cell. This information may be introduced either in vitro into a cell extracted from the organ and then reinjected into the body, or in vivo, directly into the target tissue. As a molecule of high molecular weight and of negative charge, DNA has difficulty in spontaneously crossing phospholipid cell membranes. Various vectors are thus used in order to enable gene transfer to take place: viral vectors, on the one hand, and natural or synthetic chemical and/or biochemical vectors, on the other hand.

Viral vectors (retroviruses, adenoviruses, adeno-associated viruses, etc.) are very effective, in particular for crossing membranes, but present a certain number of risks such as pathogenicity, recombination, replication, immunogenicity, etc.

Chemical and/or biochemical vectors allow these risks to be avoided (for reviews, see Behr, 1993, Cotten and Wagner 1993). These are, for example, cations (calcium phosphate, DEAE-dextran, etc.) which act by forming precipitates with DNA, which may be "phagocytosed" by the cells. They may also be liposomes in which the DNA is incorporated and which fuse with the plasma membrane. Synthetic gene-transfer vectors are generally lipids or cationic polymers which complex the DNA and form with it a particle bearing positive surface charges. As illustrations of vectors of this type, mention may be made in particular of dioctadecyla-midoglycylspermine (DOGS, Transfectam™) or N-[1-(2,3-dioleyloxy)propyl]-N,N,N-trimethylammonium (DOTMA, Lipofectin™).

However, the use of chemical and/or biochemical vectors or naked DNA implies the possibility of producing large amounts of DNA of pharmacological purity. The reason for this is that in gene therapy techniques, the medicinal product consists of the DNA itself and it is essential to be able to manufacture, in suitable amounts, DNAs having properties which are appropriate for therapeutic use in man.

In the case of non-viral vectorology, the vectors used are plasmids of bacterial origin. The plasmids generally used in gene therapy carry (i) an origin of replication, (ii) a marker gene such as a gene for resistance to an antibiotic (kanamycin, ampicillin, etc.) and (iii) one or more trans-genes with sequences necessary for their expression (enhancer(s), promoter(s), polyadenylation sequences, etc.).

However, the technology currently available is not entirely satisfactory.

On the one hand, the risk remains of dissemination in the body. Thus, a bacterium which is present in the body can, at low frequency, receive this plasmid. There is a greater likelihood of this taking place if it involves an in vivo gene therapy treatment in which the DNA may be disseminated in the body of the patient and may come into contact with bacteria which infect this patient or bacteria of the commensal flora. If the bacterium receiving the plasmid is an enterobacterium, such as E. coli, this plasmid can be replicated. Such an event then leads to dissemination of the therapeutic gene. Insofar as the therapeutic genes used in gene therapy treatments can code, for example, for a lymphokine, a growth factor, an anti-oncogene or a protein whose function is defective in the host and which thus makes it possible to correct a genetic defect, the dissemination of some of these genes could have unforeseeable and worrying effects (for example if a pathogenic bacterium acquired a human growth factor gene).

On the other hand, the plasmids generally used in non-viral gene therapy also possess a marker for resistance to an antibiotic (ampicillin, kanamycin, etc.). The bacterium acquiring such a plasmid thus has an undeniable selective advantage since any antibiotic therapy, using an antibiotic from the same family as that which selects the plasmid resistance gene, will lead to selection of the plasmid in question. In this respect, ampicillin belongs to the β-lactams, which is the family of antibiotics which is most frequently used worldwide. The use in bacteria of selection markers which are not antibiotic-resistance genes would thus be particularly advantageous. This would avoid the selection of bacteria which may have received a plasmid carrying such a marker.

It is thus particularly important to seek to limit the dissemination of therapeutic genes and resistance genes as much as possible.

The subject of the present invention is specifically to propose novel DNA molecules which can be used in gene therapy or for the production of recombinant proteins in vitro and which replicate only in cells which can complement certain functions of these non-viral vectors.

The invention also relates to a particularly effective method for preparing these DNA molecules.

The DNA molecules claimed have the advantage of removing the risks associated with dissemination of the plasmid, such as (1) replication and dissemination, which can lead to uncontrolled overexpression of the therapeutic gene, (2) dissemination and expression of resistance genes. The genetic information contained in the DNA molecules according to the invention effectively comprises the therapeutic gene(s) and the signals for regulating its (their) expression, a functional conditional origin of replication which greatly limits the host cell spectrum of this plasmid, a selection marker of reduced size which is preferably different from a gene which imparts resistance to an antibiotic and, where appropriate, a DNA fragment which allows the resolution of plasmid multimers. The probability of these molecules (and thus the genetic information which they contain) being transferred to a microorganism, and maintained stably, is very limited.

Lastly, the vectors according to the invention, also referred to as miniplasmids on account of their circular structure, their reduced size and their supercoiled form, have the following additional advantages: on account of their size which is reduced in comparison with the ColE1-derived plasmids used conventionally, the DNA molecules according to the invention potentially have better in vivo bioavailability. In particular, they have improved capacities of cell penetration and distribution. Thus, it is acknowledged that the diffusion coefficient in tissues is inversely proportional to the molecular weight (Jain, 1987). Similarly, in the cell, high molecular weight molecules have poorer permeability across the plasma membrane. In addition, in order for the plasmid to pass into the nucleus, which is essential for its expression, the high molecular weight is also a disadvantage, the nuclear pores imposing a size limit for diffusion into the nucleus (Landford et al., 1986). The reduction in size of the non-therapeutic parts of the DNA molecule (origin of replication and selection gene in particular) according to the invention also makes it possible to decrease the size of the DNA molecules. The part which allows the replication and selection of this plasmid in the bacterium (1.1 kb) is decreased by a factor of 3, counting, for example, 3 kb for the origin of replication and the resistance marker vector part. This decrease (i) in molecular weight and (ii) in negative charge imparts improved tissue, cellular and nuclear bioavailability and diffusion to the molecules of the invention.

More precisely, the present invention relates to a circular DNA molecule, which is useful in gene therapy, this molecule comprising at least one nucleic acid sequence of interest, characterized in that the region which allows its replication comprises an origin of replication whose functionality in a host cell requires the presence of at least one specific protein which is foreign to the said host cell.

This DNA molecule may be in single- or double-stranded form and advantageously possesses a supercoiled form.

For the purposes of the present invention, the host cells used can be of various origins. They can be eukaryotic or prokaryotic cells. According to a preferred embodiment of the invention, they are prokaryotic cells.

The replication of bacterial plasmids conventionally requires the presence of at least one protein, which is coded for by the host cell, of the RNA polymerase, Rnase, DNA polymerase, etc. type. For the reasons already explained above, it is not possible to overcome entirely, with this type of replication, any possible risks of dissemination in the treated organism. Advantageously, the functionality of the origin of replication of the DNA molecule according to the invention requires the presence of a specific protein which is foreign to the host cell. The significance of this characteristic is to reduce the host spectrum of the claimed plasmid to specific strains that express this initiator protein. The DNA molecule developed within the context of the present invention thus advantageously possesses a so-called conditional origin of replication.

The conditional origin of replication used according to the present invention may originate from plasmids or bacteriophages which share the following characteristics: they contain in their origin of replication repeat sequences, or iterons, and they code for at least one replication-initiating protein (Rep) which is specific to them. By way of example, mention may be made of the conditional replication systems of the following plasmids and bacteriophages:

| plasmid or bacteriophage | specific initiator protein |
|---|---|
| RK2 (Stalker et al., 1981) | TrfA |
| R1 (Ryder et al., 1981) | RepA |
| pSC101 (Vocke and Bastia, 1983) | RepA |
| F (Murotsu et al., 1981) | protein E |
| Rts1 (Itoh et al., 1982, 1987) | RepA |
| RSF1010 (Miao et al., 1995) | RepC |
| P1 (Abeles et al., 1984) | RepA |
| P4 (Flensburg and Calendar, 1987) | alpha protein |
| lambda (Moore et al., 1981) | protein O |
| phi 82 (Moore et al., 1981) | protein O from phi 82 |
| phi 80 | protein O from phi 80 |

According to a preferred embodiment of the invention, the origin of replication used in the DNA molecules claimed is derived from a natural *E. coli* plasmid referred to as R6K.

The replication functions of R6K are grouped together in a 5.5 kbp DNA fragment (FIG. 1) comprising 3 origins of replication α, β and γ (γ and β providing 90% of the replication) and an operon coding for the π replication-initiator proteins and the protein Bis. The minimum amount of genetic information required to maintain this plasmid at its characteristic number of copies (15 copies per genome) is contained in two elements: the 400 bp of ori γ and the gene pir, whose product is the π initiator protein.

Ori γ may be divided into two functional parts: the core part and the activator element (FIG. 1). The core part, which is essential for replication, contains the iterons (7 direct repeats of 22 bp) represented in SEQ ID No. 1 to which the π protein becomes bound, and flanking segments, which are targets of the host proteins (IHF, DnaA).

According to a preferred mode of the invention, the origin of replication of the vector claimed consists entirely or partially of this γ origin of replication of the plasmid R6K and more preferably, entirely or partially of SEQ ID No. 1 or one of its derivatives.

For the purposes of the present invention, the term derivative denotes any sequence which differs from the sequence considered on account of degeneracy of the genetic code, obtained by one or more modifications of genetic and/or chemical nature, as well as any sequence which hybridizes with these sequences or fragments thereof and whose product possesses the activity indicated with regard to the replication-initiator protein, π. The term modification of the genetic and/or chemical nature may be understood to refer to any mutation, substitution, deletion, addition and/or modification of one or more residues. The term derivative also comprises the sequences homologous with the sequence considered, derived from other cellular sources and in particular cells of human origin, or from other organisms, and possessing an activity of the same type. Such homologous sequences may be obtained by hybridization experiments. The hybridizations may be performed starting with nucleic acid libraries, using the native sequence or a fragment thereof as probe, under conventional conditions of stringency (Maniatis et al., cf. General techniques of molecular biology), or, preferably, under conditions of high stringency.

Figure 2:
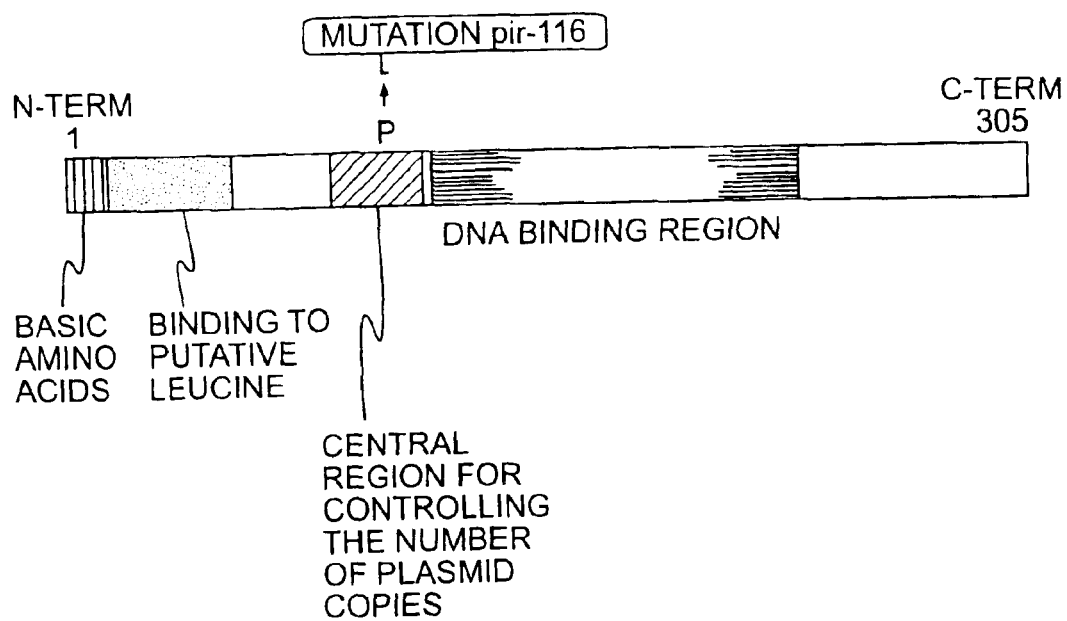

The origin of replication described above, which has the advantage of being of very limited size, is functional solely in the presence of a specific initiator protein, protein Pi, produced by the gene pir (SEQ ID No. 2). Since this protein can act in trans, it is possible to physically dissociate the ori gamma from the pir gene, which may be introduced into the genome of the cell which is chosen as the specific host for these plasmids. Mutations in π may alter its inhibitory functions (Inuzuka and Wada, 1985) and lead to an increase in the number of copies of the R6K derivatives, up to more than 10 times the initial number of copies. These substitutions are all within a domain of 40 amino acids, which therefore appears to be responsible for the control by π of the number of plasmid copies (FIG. 2).

According to an advantageous embodiment of the present invention, the π protein, expressed in the host cell, results from the expression of the gene represented in SEQ ID No. 2 or one of its derivatives as defined above and more particularly of the gene pir 116 which comprises a mutation when compared with the pir gene. This mutation corresponds to the replacement of a proline by a leucine. In this context, the number of copies of the R6K derivatives is about 250 copies per genome.

Besides a conditional origin of replication as defined above, the DNA molecules claimed contain a region comprising one (or more) gene(s) which make it possible to ensure selection of the DNA molecule in the chosen host.

This may be a conventional marker of gene type which imparts resistance to an antibiotic, such as kanamycin, ampicillin, chloramphenicol, streptomycin, spectinomycin, lividomycin or the like.

However, according to a preferred embodiment of the invention, this region is different from a gene which imparts resistance to an antibiotic. It may thus be a gene whose product is essential for the viability of the host envisaged, under defined culturing conditions. It may be, for example:
- a gene coding for a suppressor tRNA, of natural or synthetic origin. This is, more preferably, an amber codon tRNA (TAG)
- a gene whose product is necessary for metabolism of the cell, under certain culturing conditions, namely a gene involved in the biosynthesis of a metabolite (amino acid, vitamin, etc.), or a catabolism gene which makes it possible to assimilate a substance present in the culture medium (specific nitrogen or carbon source), etc.

According to a preferred mode of the invention, this region contains an expression cassette of a gene coding for a suppressor tRNA for specific codons. This latter may be chosen, in particular, from those coding for phenylalanine, cysteine, proline, alanine and histidine bases. It is more particularly a suppressor tRNA for amber codons (TAG).

In this particular case, the system used to select, in the host cells, the DNA molecules which are the subject of the present invention includes two elements: 1) on the DNA molecule, a gene coding for a suppressor transfer RNA for the amber codon (TAG) which constitutes the selection marker, known as (sup) gene and 2) a specific host, one of whose genes, which is essential under certain culture conditions, contains an amber TAG codon. This cell may grow, under the culture conditions for which the product of the gene containing the TAG codon is essential, only if the plasmid allowing the expression of sup is present in the cell. The culture conditions thus constitute the pressure for selection of the DNA molecule. The sup genes used may be of natural origin (Glass et al., 1982) or may originate from a synthetic construction (Normanly et al., 1986, Kleina et al., 1990).

Such a system offers great flexibility insofar as, depending on the gene containing an amber mutation, it is possible to determine various selective media. In the bacterium *Lactococcus lactis* for example, the amber codon is located in a purine biosynthesis gene. This allows the selection of the plasmid carrying the gene coding for the suppressor tRNA when the bacteria multiply in milk. Such a marker has the advantage of being very small and of containing no "foreign" sequences, originating from phages or transposons.

According to a particular embodiment of the invention, the DNA molecule also comprises a DNA fragment, the target for site-specific recombinases, which allows the resolution of plasmid multimers.

Thus, such a fragment, introduced on to a DNA molecule which is circular and whose origin of replication is, for example, ori gamma, allows the resolution of multimers of such a plasmid. Such multimers are observed, in particular, when the DNA molecule is prepared in a strain carrying a mutated allele of pir, such as pir-116, which makes it possible to increase the number of copies of the R6K derivatives.

This recombination may be achieved by means of various systems which entail site-specific recombination between sequences. More preferably, the site-specific recombination of the invention is obtained by means of specific intramolecular recombination sequences which are capable of recombining with each other in the presence of specific proteins, generally referred to as recombinases. In this specific case, these are the recombinases XerC and XerD. For this reason, the DNA molecules according to the invention generally also comprise a sequence which allows this site-specific recombination. The specific recombination system present in the genetic constructions according to the invention (recombinases and specific recognition site) may be of different origins. In particular, the specific sequences and the recombinases used may belong to different structural classes, and in particular to the transposon Tn3 resolvase family or to the bacteriophage lambda integrase family. Among the recombinases belonging to the transposon Tn3 family, mention may be made in particular of the resolvase of transposon Tn3 or of transposons Tn21 and Tn522 (Stark et al., 1992); the Gin invertase of bacteriophage mu or alternatively plasmid resolvases, such as that of the par fragment of RP4 (Abert et al., Mol. Microbiol. 12 (1994) 131). Among the recombinases belonging to the bacteriophage λ integrase family, mention may be made in particular of the integrase of the phages lambda (Landy et al., Science 197 (1977) 1147), P22 and φ80 (Leong et al., J. Biol. Chem. 260 (1985) 4468), HP1 of *Haemophilus influenzae* (Hauser et al., J. Biol. Chem. 267 (1992) 6859), the Cre integrase of phage P1, the integrase of plasmid pSAM2 (EP 350 341) or alternatively the FLP recombinase of the 2μ plasmid and the XerC and XerD recombinases from *E. coli*.

Preferably, the DNA molecules which form the subject of the present invention contain the fragment cer from the natural *E. coli* plasmid ColE1. The cer fragment used is a 382 bp HpaII fragment from ColE1 which has been shown to bring about, in cis, the resolution of plasmid multimers (Summers et al., 1984; Leung et al., 1985). It is also possible to use a HpaII-TaqI fragment of smaller size (280 bp) or a smaller fragment (about 220 bp), contained in the HpaII fragment, which fragments possess the same properties (Summers and Sherratt, 1988). This resolution takes place by way of a specific intramolecular recombination, which involves four proteins encoded by the genome of *E. coli*: ArgR, PepA, XerC and XerD (Stirling et al., 1988, 1989; Colloms et al., 1990, Blakely et al., 1993).

In this respect, it [lacuna] particularly advantageous to use all or part of the cer fragment of ColE1 or one of its derivatives as defined above.

According to an implementation variant, the DNA molecules of the invention may also comprise a sequence capable of interacting specifically with a ligand. Preferably, this is a sequence capable of forming, by hybridization, a triple helix with a specific oligonucleotide. This sequence thus makes it possible to purify the molecules of the invention by selective hybridization with a complementary oligonucleotide immobilized on a support (see application WO 96/18744). The sequence can be positioned at any site in the DNA molecule of the invention, provided that it does not affect the functionality of the gene of interest and of the origin of replication.

As a DNA molecule representative of the present invention, the plasmid pXL2774 and its derivatives may be claimed most particularly. For the purposes of the invention, the term derivative is understood to refer to any construction derived from pXL2774 and containing one or more genes of interest other than the luciferase gene. Mention may also be made of the plasmids pXL3029 and 3030 containing an expression cassette of a therapeutic gene and a sequence capable of interacting specifically with a ligand.

The present invention also relates to the development of a process for the construction of specific host cells, which are particularly effective for the production of these therapeutic DNA molecules.

Another subject of the present invention relates to a process for the production of a circular DNA molecule, characterized in that a host cell is cultured containing at least one DNA molecule as defined above and a protein, which may or may not be expressed in situ, which conditions the functionality of the origin of replication of the said DNA molecule, which is specific and which is foreign to the said host cell, under conditions which allow the selection of host cells transformed by the said DNA molecules.

More preferably, the protein which conditions the functionality of the origin of replication of the DNA molecule is expressed in situ from a corresponding gene. The gene coding for the replication-initiating protein may be carried by a subsidiary replicon, which is compatible with the derivatives of the conditional origin of replication used or which may be introduced into the genome of the host cell by recombination, by means of a transposon, a bacteriophage or any other vector. In the particular case in which the gene expressing the protein is placed on a subsidiary replicon, the latter also contains a promoter region for functional transcription in the cell, as well as a region which is located at the 3' end and which specifies a transcription termination signal. As regards the promoter region, this may be a promoter region which is naturally responsible for expressing the gene under consideration when the latter is capable of functioning in the cell. It may also be a case of regions of different origin (responsible for expressing other proteins), or even of synthetic origin. In particular, it may be a case of promoter sequences for prokaryotic or bacteriophage genes. For example, it may be a case of promoter sequences obtained from the cell genome.

As genes coding for the replication-initiating protein, use may be made either of wild-type genes or of mutated alleles which make it possible to obtain an increased number of copies of the plasmids (or derivatives) specific for the initiator protein which conditions the functionality of the origin of replication used in the DNA molecule.

Such mutants have been described in particular for the plasmids R6K (Inuzuka and Wada, 1985; Greener et al., (1990), Rts1 (Terawaki and Itoh, 1985, Terawaki et al., 1990; Zeng et al., 1990), F (Seelke et al., 1982; Helsberg et al., 1985; Kawasaki et al., 1991), RK2 (Durland et al., 1990; Haugan et al., 1992, 1995), pSC101 (Xia et al., 1991; Goebel et al., 1991; Fang et al., 1993).

In the particular case in which the DNA molecule used possesses an origin of replication derived from the plasmid R6K, the initiator protein is a derivative of the π protein of this same plasmid. It is particularly advantageous to express a mutated form of this protein which is capable of increasing the number of initial copies appreciably. To do this, the gene incorporated into the host cell is preferably represented by all or part of the sequence represented in SEQ ID No. 2 or one of its derivatives and more preferably by the pir 116 gene. The associated mutation corresponds to the replacement of a proline by a leucine. According to a particular embodiment of the invention, this pir 116 gene is directly incorporated into the host cell genome.

Advantageously, one of the genes of the specific host cell, which is essential under the culture conditions chosen, contains a specific codon which is recognizable by the selected suppressor tRNA in the DNA molecule. According to a preferred mode of the invention, this is an amber TAG codon. In this particular case, the cell may grow, under culture conditions for which the product of the gene containing the TAG codon is essential, only if the plasmid allowing the expression of sup is present in the host cell. The culture conditions thus constitute the pressure for selection of the DNA molecule.

Preferably, the gene containing the amber codon is a gene involved in the biosynthesis of an amino acid, arginine. This gene, argE, codes for an N-acetylornithinase (Meinnel et al., 1992) and in this case contains a TAG codon corresponding to a point mutation Gln-53 (CAG)->TAG; the pressure for selection of the plasmid carrying the sup gene is then provided by culturing in minimal M9 medium (Maniatis et al., 1989). However, this could also be, for example, a gene for biosynthesis of a vitamin or a nucleic acid base, or alternatively a gene which allows a specific nitrogen or carbon source to be used or any other gene whose functionality is essential for cellular viability under the chosen culture conditions.

The host cell is preferably chosen from *E. coli* strains and is more preferably represented by the strain *E. coli* XAC-1.

According to a specific embodiment of the invention, the host cell used in the claimed process is a cell of the *E. coli* strain XAC-1, containing the pir 116 gene in its genome and transformed by the plasmid pXL2774 or one of its derivatives.

According to an advantageous variant of the invention, the host cell used in the process claimed is a prokaryotic cell in which the endA1 gene or a homologous gene is inactivated. The endA gene codes for endonuclease I of *E. coli*. This periplasmic enzyme has a non-specific activity of cleaving double-stranded DNA (Lehman, I. R., G. G. Roussos and E. A. Pratt (1962) J. Biol. Chem. 237: 819–828; Wright M. (1971) J. Bacteriol. 107: 87–94). A study carried out on various strains of *Escherichia coli* (wild-type or endA) showed that the degradation of plasmid DNA incubated in extracts of these bacterial strains existed in the endA+ strains but not in the endA mutants. (Wnendt S. (1994) BioTechniques 17: 270–272). The quality of the plasmid DNA isolated from endA+ strains or from endA mutants was studied by the company Promega using their purification system (Shoenfeld, T., J. Mendez, D. Storts, E. Portman, B.†Patterson, J. Frederiksen and C. Smith. 1995. Effects of bacterial strains carrying the endA1 genotype on DNA quality isolated with Wizard plasmid purification systems. Promega notes 53). Their conclusion is as follows: the quality of the DNA prepared from endA mutants is, overall, better than that of DNA prepared in the endA+ strains tested.

The quality of the plasmid DNA preparations is thus affected by any contamination with this endonuclease (relatively long-term degradation of the DNA).

The deletion or mutation of the endA gene can be envisaged without difficulty insofar as the mutants no longer having this endonuclease activity behave on the whole like wild-type bacteria (Dürwald, H. and H. Hoffmann-Berling (1968) J. Mol. Biol. 34: 331–346).

The endA1 gene can be inactivated by mutation, total or partial deletion, disruption, etc. Inactivation of the endA gene of the *E. coli* strain chosen to produce the pCOR plasmids can be achieved more particularly by transferring, by means of the P1 bacteriophage, the ΔendA::$Tc^R$ deletion described by Cherepanov and Wackernagel (Cherepanov, P. P. and W. Wackernagel. 1995. Gene disruption in *Escherichia coli*: $Tc^R$ and $Km^R$ cassettes with the option of Flp-catalyzed excision of the antibiotic-resistance determinant. Gene 158:9–14) or by exchanging the wild-type allele present in the genome of the bacterium of interest with a mutated or deleted allele of endA, by homologous recombination. The use of this type of strain in the context of the present invention makes it possible advantageously to improve the quality of the DNA produced.

The invention also relates to any recombinant cell containing a DNA molecule as defined above. This may be a cell of various origins, of eukaryotic, prokaryotic, etc. type.

These cells are obtained by any technique known to those skilled in the art which allows the introduction of the said plasmid into a given cell. Such a technique may be, in particular, transformation, electroporation, conjugation, fusion of protoplasts or any other technique known to those skilled in the art.

The DNA molecules according to the invention may be used in any application of vaccination or of gene and cell therapy for transferring a gene to a given cell, tissue or organism, or for the production of recombinant proteins in vitro.

In particular, they may be used for direct in vivo administration or for the modification of cells in vitro or ex vivo, for the purpose of implanting them into a patient.

In this respect, another subject of the present invention relates to any pharmaceutical composition comprising at least one DNA molecule as defined above. This molecule may or may not be associated therein with a chemical and/or biochemical transfection vector. This may in particular involve cations (calcium phosphate, DEAE-dextran, etc.) or liposomes. The associated synthetic vectors may be cationic polymers or lipids. Examples of such vectors which may be mentioned are DOGS (Transfectam™) or DOTMA (lipofectin™).

The pharmaceutical compositions according to the invention may be formulated for the purpose of topical, oral, parenteral, intranasal, intravenous, intramuscular, subcutaneous, intraocular, transdermal, etc. administrations. The claimed plasmid is preferably used in an injectable form or in application. It may be mixed with any vehicle which is pharmaceutically acceptable for an injectable formulation, in particular for a direct injection to the site to be treated. This may involve, in particular, sterile, isotonic solutions or dry compositions, in particular freeze-dried compositions, which, by addition, depending on the case, of sterilized water or of physiological saline, allow injectable solutions to be made up. This may in particular involve Tris or PBS buffers diluted in glucose or in sodium chloride. A direct injection into the affected region of the patient is advantageous since it allows the therapeutic effect to be concentrated at the level of the affected tissues. The doses used may be adapted as a function of various parameters, and in particular as a function of the gene, the vector, the mode of administration used, the pathology concerned or the desired duration of the treatment.

The DNA molecules of the invention may contain one or more genes of interest, that is to say one or more nucleic acids (synthetic or semi-synthetic DNA, gDNA, cDNA, etc.) whose transcription and, possibly, whose translation in the target cell generate products of therapeutic, vaccinal, agronomic or veterinary interest.

Among the genes of therapeutic interest which may be mentioned more particularly are genes coding for enzymes, blood derivatives, hormones and lymphokines: interleukins, interferons, TNF, etc. (FR 92/03120), growth factors, neurotransmitters or their precursors or synthetic enzymes, and trophic factors: BDNF, CNTF, NGF, IGF, GMF, aFGF, bFGF, NT3, NT5, etc.; apolipoproteins: ApoAI, ApoAIV, ApoE, etc. (FR 93/05125), dystrophin or a minidystrophin (FR 91/11947), tumour-suppressing genes: p53, Rb, Rap1A, DCC, k-rev, etc. (FR 93/04745), genes coding for factors involved in coagulation: factors VII, VIII, IX, etc., suicide genes: thymidine kinase, cytosine deaminase, etc.; or alternatively all or part of a natural or artificial immunoglobulin (Fab, ScFv, etc.), an RNA ligand (WO 91/19813), etc. The therapeutic gene may also be an antisense sequence or gene, whose expression in the target cell makes it possible to control the expression of genes or the transcription of cellular mRNAs. Such sequences may, for example, be transcribed, in the target cell, into RNAs which are complementary to cellular mRNAs and thus block their translation into protein, according to the technique described in patent EP 140,308.

The gene of interest may also be a vaccinating gene, that is to say a gene coding for an antigenic peptide, capable of generating an immune response in man or animals, for the purpose of producing vaccines. These antigenic peptides may in particular be specific antigenic peptides of Epstein-Barr virus, HIV virus, hepatitis B virus (EP 185,573), or pseudorabies virus, or alternatively specific antigenic peptides of tumours (EP 259,212).

Generally, in the DNA molecules of the invention, the gene of therapeutic, vaccinal, agronomic or veterinary interest also contains a promoter region for functional transcription in the target organism or cell, as well as a region located at the 3' end which specifies a transcription termination signal and a polyadenylation site. As regards the promoter region, it may be a promoter region naturally responsible for expression of the gene under consideration when this region is capable of functioning in the cell or the organism concerned. The promoter regions may also be regions of different origin (responsible for the expression of other proteins) or even of synthetic origin. In particular, they may be promoter sequences from eukaryotic or viral genes. For example, they may be promoter sequences obtained from the genome of the target cell. Among the eukaryotic promoters which may be used are any promoter or derived sequence which stimulates or suppresses the transcription of a gene in a specific or non-specific, inducible or non-inducible, strong or weak manner. The eukaryotic promoters may in particular be ubiquitous promoters (promoters of the genes for HPRT, PGK, $\alpha$-actin, tubulin, etc.), intermediate filament promoters (promoters of the genes for GFAP, desmin, vimentin, neurofilaments, keratin, etc.), therapeutic gene promoters (for example the promoters of the genes for MDR, CFTR, factor VIII, ApoAI, etc.) tissue-specific promoters (promoters of the genes for pyruvate kinase, villin, intestinal fatty acid-binding protein, $\alpha$-actin of smooth muscle, etc.) or alternatively promoters which respond to a stimulus (steroid hormone receptor, retinoic acid receptor, etc.). Similarly, they may be promoter sequences obtained from the genome of a virus, such as, for example, the promoters of the adenovirus E1A and MLP genes, the CMV early promoter or alternatively the LTR promoter of RSV, etc. In addition, these promoter regions may be modified by addition of activating or regulatory sequences or sequences which allow tissue-specific expression or expression which is predominantly tissue-specific.

Moreover, the gene of interest may also contain a signal sequence which directs the synthesized product into the secretory pathways of the target cell. This signal sequence may be the natural signal sequence of the synthesized product, but it may also be any other functional signal sequence or an artificial signal sequence.

Depending on the gene of interest, the DNA molecules of the invention may be used for the treatment or prevention of several pathologies, including genetic diseases (dystrophy, cystic fibrosis, etc.), neurodegenerative diseases (Alzheimer's disease, Parkinson's disease, ALS, etc.), cancers, pathologies associated with coagulation disorders or with dyslipoproteinaemias, pathologies associated with viral infections (hepatites, AIDS, etc.), or in the agronomic and veterinary fields, etc.

Moreover, the present invention also relates to the use of conditional replication DNA molecules for the production of recombinant proteins. Bacteria can be used to produce proteins of various origins, eukaryotic or prokaryotic. Among the bacteria, *E. coli* constitutes the organism of choice for expressing heterologous genes on account of its ease of manipulation, the large number of expression systems available and the large amounts of proteins which can be obtained. It is understood that the system of the invention can be used in other organisms, the tropism being determined by the nature of the origin of replication, as indicated above. For this use, the nucleic acid sequence of interest comprises a coding region under the control of expression signals that are appropriate for the host chosen, in particular a prokaryotic host. These may be, for example, Plac, Ptrp, PT7, Ptrc, Ptac, PL or PR promoters, the Shine-Dalgarno sequence, etc. (this set constitutes the expression cassette). The nucleic acid sequence of interest can be any sequence coding for a protein which is of value in the fields of pharmacy, agri-foods, chemistry or agrochemistry. This may be a structural gene, a complementary DNA sequence, a synthetic or semi-synthetic sequence, etc.

The expression cassette can be introduced onto the conditional replication vector which is the subject of the invention, thus constituting a conditional replication vector which allows the expression of proteins of interest in *E. coli*. This vector has several advantages: no use of antibiotic to select it in the bacterium (reduced cost, no need for a study regarding the presence of antibiotic or of potentially toxic derived products in the finished product), virtually no probability of dissemination of the plasmid in nature (conditional origin of replication), possible fermentation in entirely defined medium. The examples given show the advantageous properties of these conditional vectors for the production of recombinant proteins.

The present invention will be described more fully with the aid of the examples which follow, which should be considered as non-limiting illustrations.

KEY TO THE FIGURES

FIG. 1: Functional organization of the region of R6K involved in replication.

FIG. 2: organization of the functional domains of the π protein of the plasmid R6k.

Figure 3:
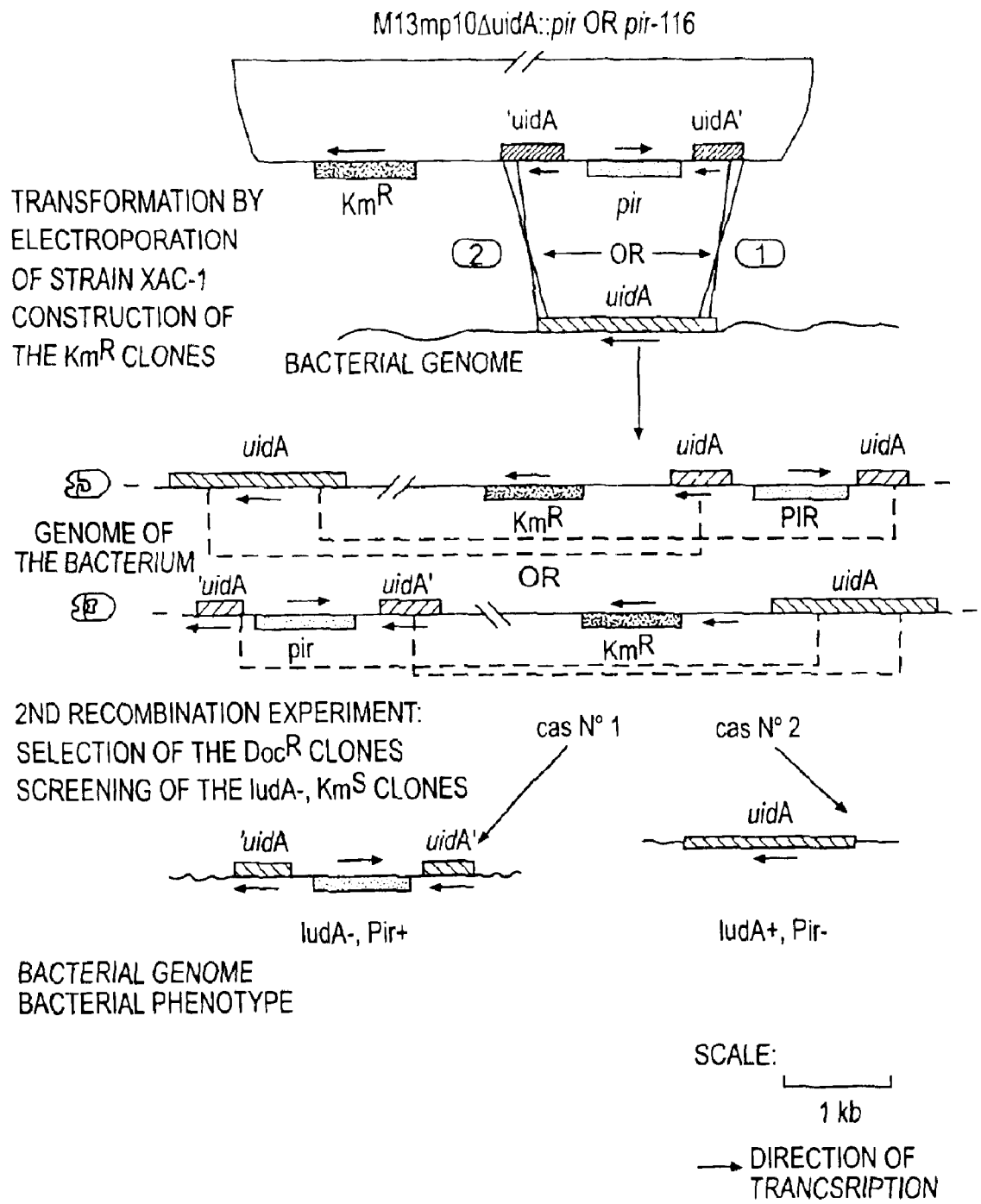

FIG. 3: Representation of the protocol for introducting the pir gene into the genome of *E. coli* XAC1.

Figure 4:
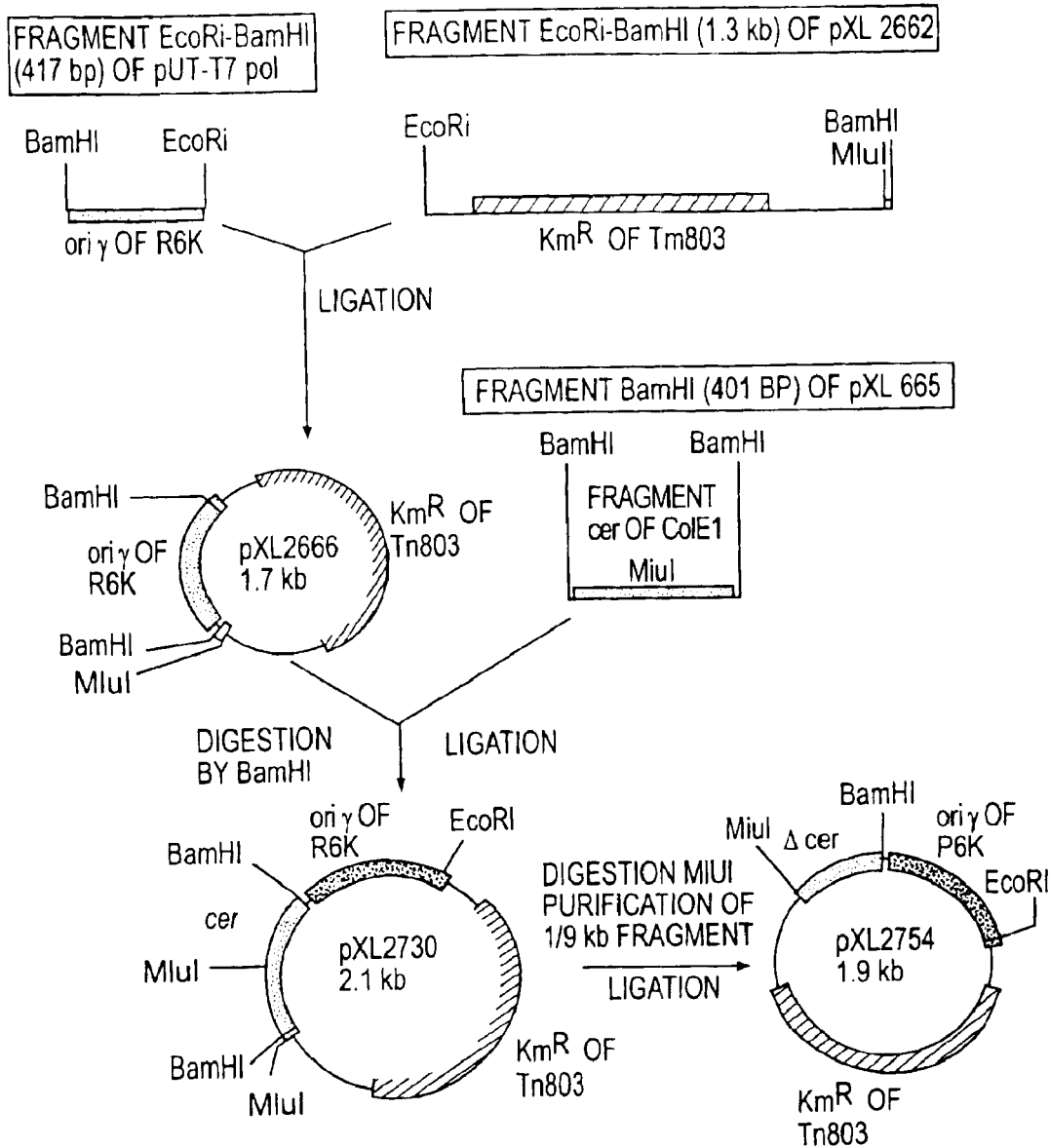

FIG. 4: Construction scheme for vectors pXL2666, 2730 and 2754.

Figure 5:
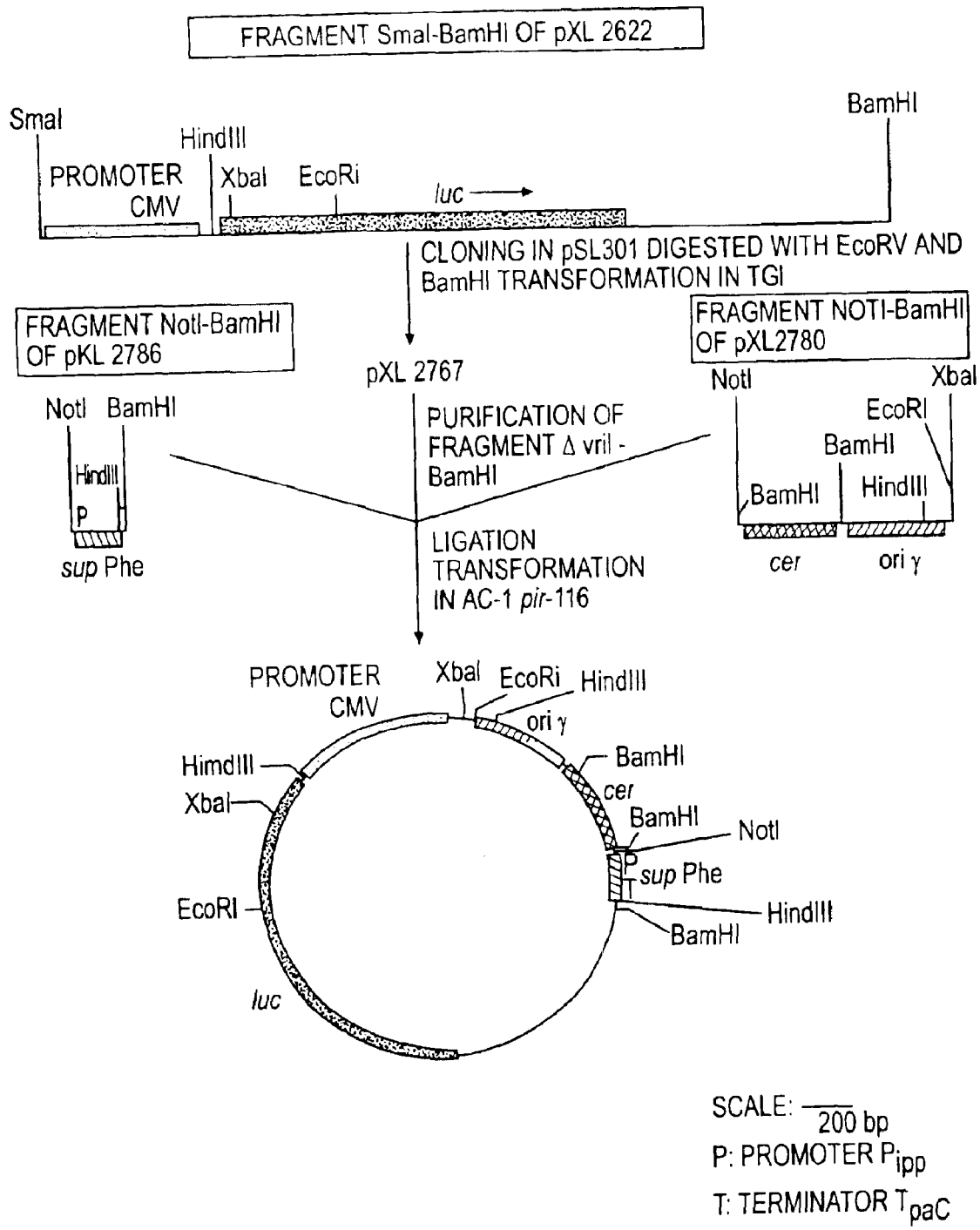

FIG. 5: Construction of pXL2774.

Figure 6:
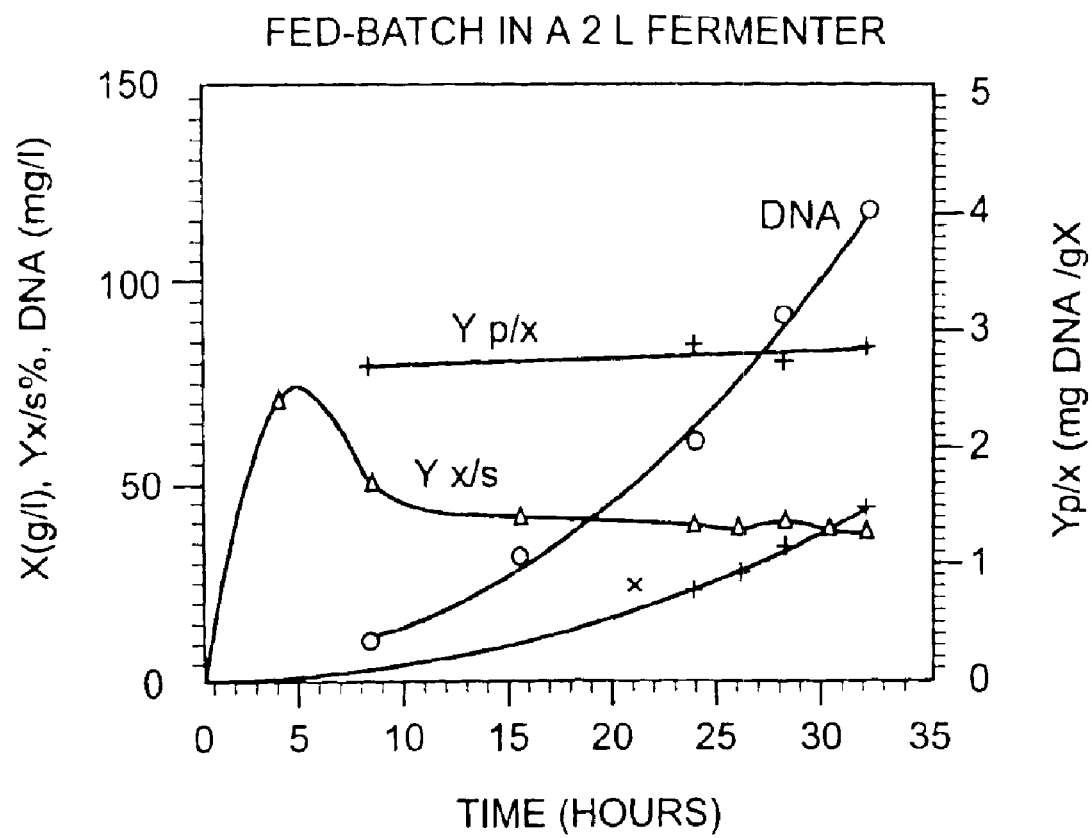

FIG. 6: Growth and production kinetics in a 2L fermenter.

Figure 7:
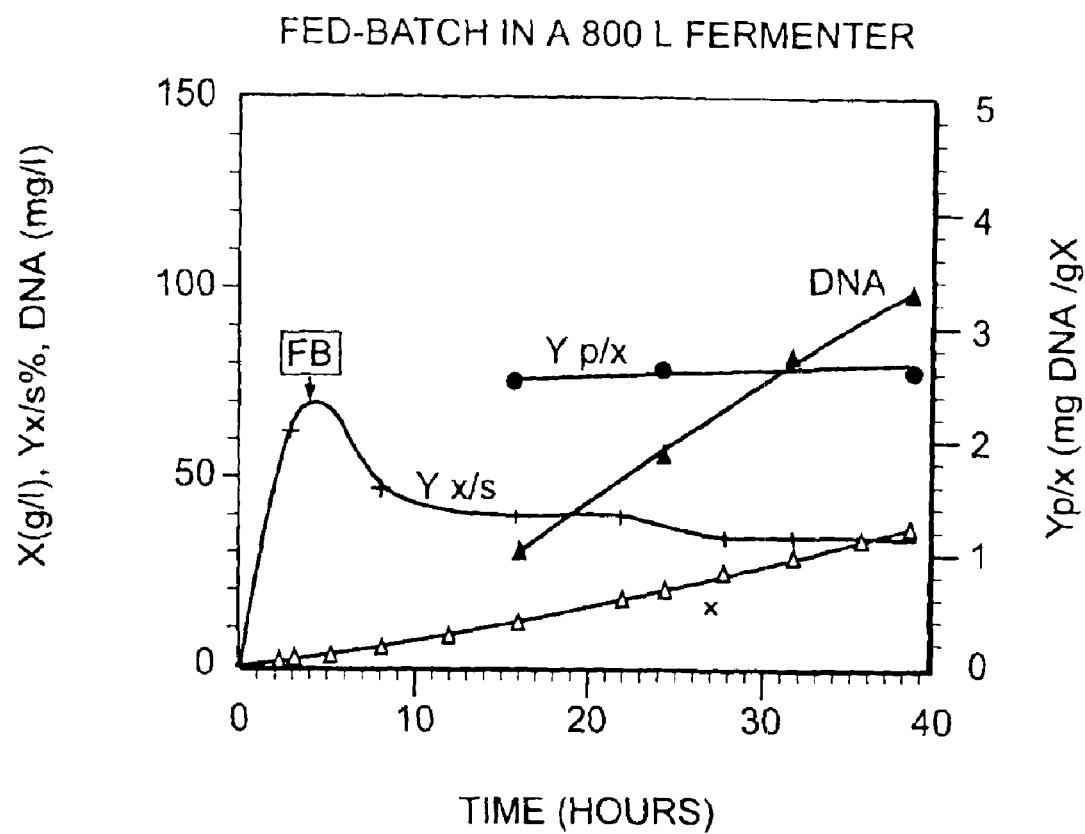

FIG. 7: Growth and production kinetics in an 800L fermenter.

Figure 8:
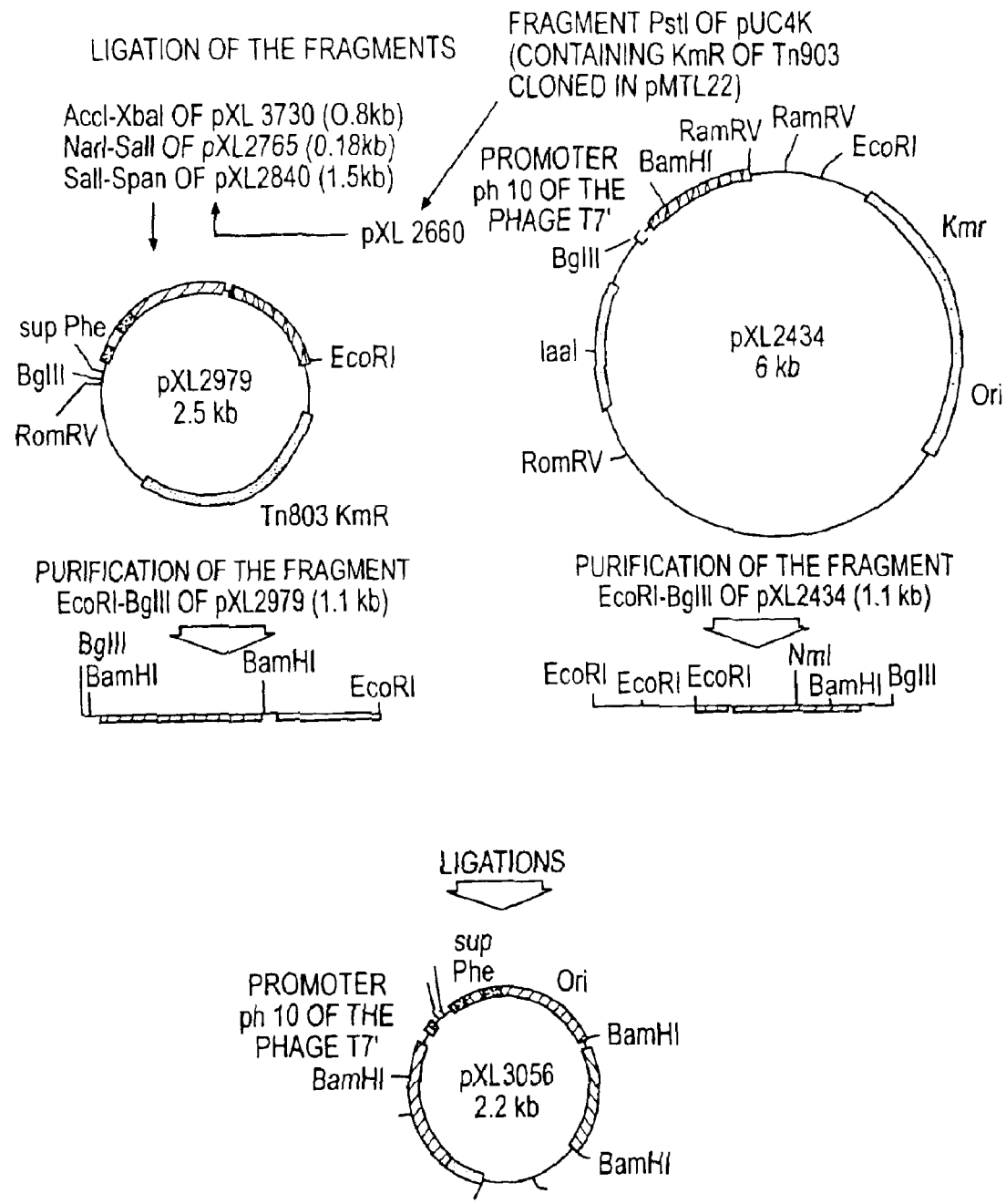

FIG. 8: Construction of pXL3056.

Figure 9:
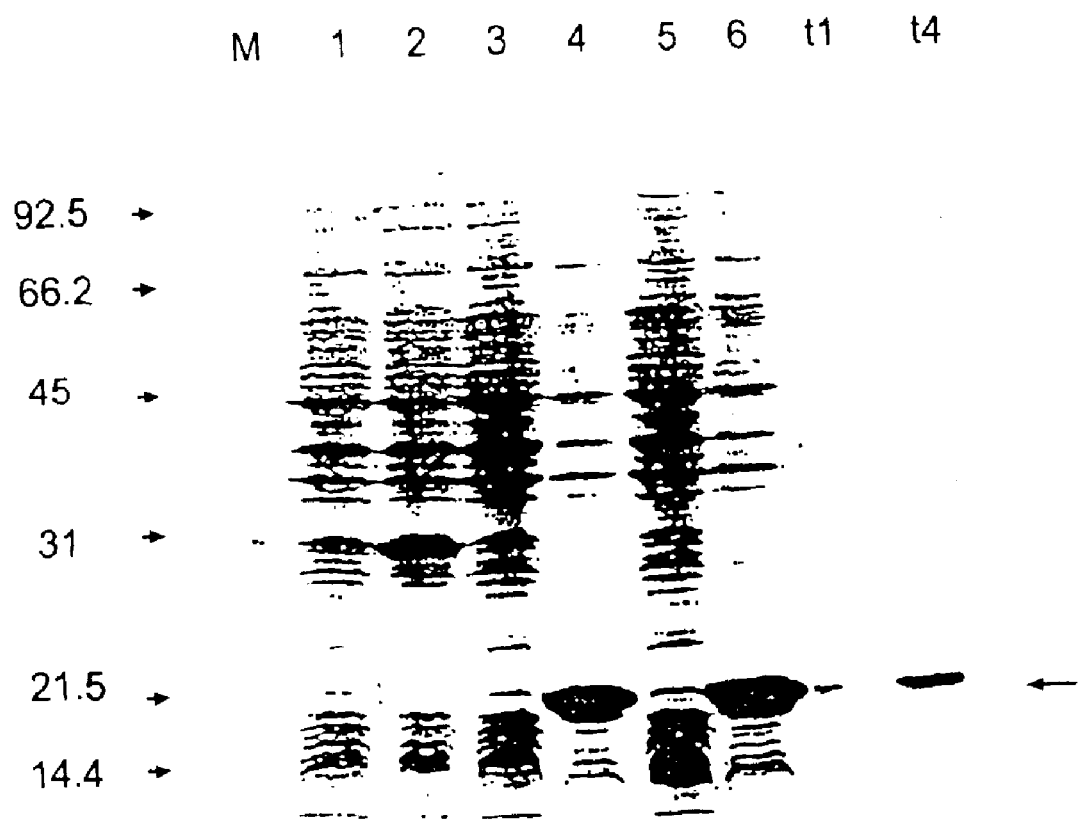

FIG. 9: Visualization of the aFGF protein produced by *E. coli* XAC-1pir-116 (pXL3056+PT7pol23) after induction. The denatured total cell extracts are deposited on 12.5%-SDS polyacrylamide gel. M: molecular mass marker (Biorad, Low range). Each band is identified by an arrow and a figure which indicates its mass in kDaltons. 1: XAC-1pir-116 (pXL3056+pUC4K) not induced; 2: XAC-1pir-116 (pXL3056+pUC4K) induced at 42° C.; 3: XAC-1pir-116 (pXL3056+PT7pol23) clone 1, not induced; 4: XAC-1pir-116 (pXL3056+PT7pol23) clone 1, induced at 42° C.; 5: XAC-1pir-116 (pXL3056+PT7pol23) clone 2, not induced; 6: XAC-1pir-116 (pXL3056+PT7pol23) clone 2, induced at 42° C.; t1: 1 μg of purified aFGF; t4: 4 μg of purified aFGF.

Figure 10:
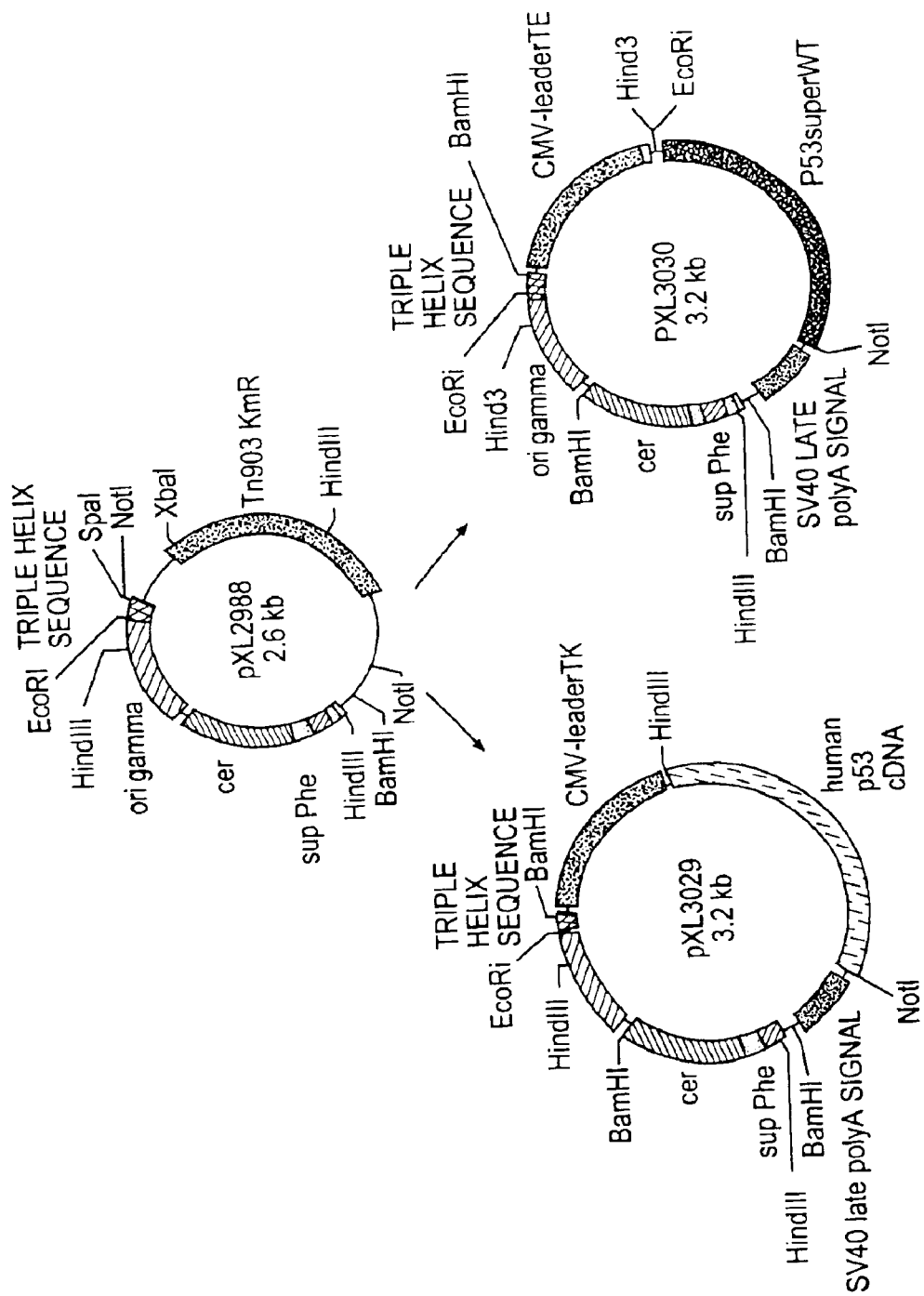

FIG. 10: Construction scheme for vectors pXL3029 and pXL3030.

I—MATERIALS AND METHODS

A) Materials

1) Culture media

Complete LB, 2XTY and SOC media and minimal M9 medium (Maniatis et al., 1989) were used. Agar media were obtained by addition of 15 g of Difco agar. Furthermore, if necessary, these media were supplemented with antibiotics (ampicillin or kanamycin) at respective concentrations of 100 mg/l and 50 mg/l. The chromogenic substrates X-Gal and X-Gluc were used at a concentration of 40 mg/l.

2) *E. coli* strains, plasmids and bacteriophages

The *E. coli* strains, plasmids and bacteriophages used are respectively identified in the examples below.

B) Methods

1) Manipulation of the DNA

The isolation of bacterial DNA (plasmid and genomic) and phage DNA (replicative form of M13), digestion with restriction endonucleases, ligation of the DNA fragments, agarose gel electrophoresis (in TBE buffer) and other standard techniques were carried out according to the manufacturers' recommendations, for the use of enzymes, or in accordance with the procedures described in "Molecular Cloning: a Laboratory Manual" (Maniatis et al., 1989).

The DNA size markers used during the electrophoreses are as follows: 1 kb ladder (BRL) for the linear fragments and the supercoiled DNA marker (Stratagene) for the undigested plasmids.

Sequencing was carried out according to the Sanger technique (Sanger et al., 1977) adapted to the automated method using fluorescent dideoxynucleotides and Taq DNA polymerase (PRISM Ready Reaction DyeDideoxy Terminator Cycle Sequencing Kit, Applied Biosystems).

The oligodeoxynucleotides used (designated by "seq+ no.", see below) were synthesized on the "Applied Biosystems 394 DNA/RNA Synthesizer" by the phosphoramidite method, using β-cyanoethyl protecting groups (Sinha et al., 1984). After synthesis, the protecting groups are removed by treatment with ammonia. Two precipitations with butanol allow the oligonucleotide to be purified and concentrated (Sawadogo et al., 1991).

Sequences of the Oligonucleotides Used for the PCR Amplification:

SEQ ID No. 3   5'-GACCAGTATTATTATCTTAATGAG-3'

SEQ ID No. 4   5'-GTATTTAATGAAACCGTACCTCCC-3'

SEQ ID No. 5   5'-CTCTTTTAATTGTCGATAAGCAAG-3'

SEQ ID No. 6   5'-GCGACGTCACCGAGGCTGTAGCCG-3'

The PCR reactions (Saïki et al., 1985) were performed under the following conditions, in a total volume of 100 μl. The reaction mixture comprises 150 ng of genomic DNA from the strain to be studied, 1 μg of each of the two oligonucleotide primers (24-mer), 10 μl of 10×PCR buffer, the composition of which is as follows "500 mM KCl, 0.1% gelatin, 20 mM $MgCl_2$, 100 mM Tris-HCl pH 7.5", and 2.5 units of Taq DNA polymerase (Amplitaq Perkin-Elmer). The PCR conditions, on the Perkin-Elmer Cetus DNA Thermal Cycler machine are as follows: 2 min at 91° C., 30 successive cycles of denaturation (1 min at 91° C.), hybridization (2 min at 42° C.) and elongation (3 min at 72° C.), and finally 5 min at 72° C. The products thus obtained, which are or are not digested with a restriction enzyme, are analysed by agarose gel electrophoresis.

Analysis of the various plasmid species by DNA topoisomerases was performed according to the following procedure: the enzymes, purified in the laboratory, are incubated for 1 hour at 37° C. The reaction mixtures (total volume: 40 µl) have the following composition: 150 ng of plasmid, 300 ng of DNA topoisomerase I or 150 ng of *E. coli* DNA gyrase, or 160 ng of *S. aureus* DNA topoisomerase IV and 20 µl of buffer specific for each enzyme. The composition of these buffers is indicated below:

| for DNA topoisomerase I: | 50 mM Tris-HCl pH 7.7, 40 mM KCl, 1 mM DTT, 100 µg/ml BSA, 3 mM MgCl$_2$, 1 mM EDTA; |
|---|---|
| for DNA topoisomerase IV: | 60 mM Tris-HCl pH 7.7, 6 mM MgCl$_2$, 10 mM DTT, 100 µg/ml BSA, 1.5 mM ATP, 350 mM potassium glutamate; |
| for DNA gyrase: | 50 mM Tris-HCl pH 7.7, 5 mM MgCl$_2$, 1.5 mM ATP, 5 mM DTT, 100 µg/ml BSA, 20 mM KCl. |

2) Transformation of *E. coli*

This was performed routinely according to the TSB (Transformation and Storage Buffer) method described by Chung and Miller (1988). For a strain such as TG1 (Gibson et al., 1984), the transformation efficiency obtained is about $10^5$–$10^6$ transformants per µg of pUC4K (Vieira and Messing; 1982). When a higher transformation efficiency was necessary, the bacteria were transformed by electroporation according to the procedure recommended by the electroporator manufacturer (Biorad). This method makes it possible to achieve efficiencies of from $10^8$ to $10^{10}$ transformants per µg of pUC4K.

3) Cellular Transfection Mediated by a Cationic Lipofectant

The cells used are NIH 3T3 mouse fibroblasts seeded the day before into 24-well plates, at a density of 50,000 cells per well. The culture medium used is DMEM medium, containing 4.5 g/l of glucose and supplemented with 10% foetal calf serum and 1% of solutions of 200 mM glutamine and antibiotics ($5.10^3$ u/ml streptomycin, $5.10^3$ µg/ml penicillin) (Gibco). The plasmid DNA (1 µg in 25 µl of 9% NaCl) is mixed, on a volume-for-volume basis, with a suspension of lipofectant. Four "lipofectant charges/DNA charges" ratios are tested: 0, 3, 6 and 9. These ratios are calculated by considering that 1 µg of plasmid DNA carries 3.1 nmol of negative charges and that the lipofectant contains 3 positive charges per molecule. After a contact time of 10 minutes to allow formation of the DNA/lipid complex, 50 µl of DNA-lipofectant mixture are introduced onto the cells in serum-free culture medium (500 µl). The cells were prerinsed twice with this same medium. Inhibition of transfection by the serum is thus avoided. After incubation (2 hours at 37° C. in the CO$_2$ incubator), 10% foetal calf serum is added to the medium. The cells are then reincubated for 24 hours.

4) Measurement of the Luciferase Activity of Eukaryotic Cells

This is carried out 24 hours after the transfection. Luciferase catalyses the oxidation of luciferin in the presence of ATP, Mg$^{2+}$ and O$_2$, with concomitant production of a photon. The total amount of light emitted, measured by a luminometer, is proportional to the luciferase activity of the sample. The reagents used are supplied by Promega (luciferase assay system) and used according to the recommended procedure. After lysis of the cells, the insoluble fraction from each extract is eliminated by centrifugation. The assay is carried out on 5 µl of supernatant, which may or may not be diluted in the cell lysis buffer.

3) Measurement of the Protein Concentration in the Cell Extracts

This is carried out according to the BCA method (Pierce) using bicinchoninic acid (Wiechelman et al., 1988). The standard BSA range is prepared in the lysis buffer (cf. III-B-4). The samples to be assayed and those of the range are pretreated, on a volume-for-volume basis, with 0.1 M iodoacetamide/0.1 M Tris buffer, pH 8.2, for 1 hour at 37° C. This treatment makes it possible to prevent interference, during the assay, of the reducing agent (DTT) present in the lysis buffer. The assay result is read at 562 nm.

EXAMPLE 1

Construction of XAD-1pir and pir-116 Hoststrains by Homologous Recombination

The strain used is the *E. coli* strain XAC-1 (Normanly et al., 1980). The argE gene of this strain advantageously includes a mutation of glutamine-53 (CAG) into the amber codon (TAG) (Meinnel et al., 1992). The argE gene belongs to the argECBH divergent operon and codes for an arginine biosynthesis enzyme, N-acetylornithinase. XAC-1 cannot therefore synthesize arginine and, consequently, grow in minimal medium. This auxotrophy will be relieved if the strain harbours a plasmid which allows the expression of a suppressor tRNA. It will thus be possible, by culturing in minimal medium, to select bacteria which carry such a plasmid. In order to allow the replication therein of plasmids derived from R6K, it was necessary to introduce, by homologous recombination, the pir gene into the genome of XAC-1. The pir gene (wild-type or mutated) is introduced at the uidA locus by exchange between the wild-type uidA gene and a copy interrupted by the pir (or pir-116) gene. The uida gene codes for β-glucuronidase, the enzyme for hydrolysis of β-glucuronides. This gene may be inactivated without any problem since it is not essential for growth in standard synthetic media, in which β-glucuronides are not used. Furthermore, the β-glucuronidase activity can be monitored by means of a chromogenic substrate, X-Gluc, whose hydrolysis releases a blue pigment.

1) Construction of a Suicide Vector Carrying the Cassette "Km$^R$-uidA::pir (or pir-116)

We used a strategy involving a single bacterial host and minimizing the modifications to the genome of the strain of interest. The phage M13mp10 (Messing et Vieira; 1982) was used as suicide vector (Blum et al., 1989). An amber mutation in the gene II, which is essential for replication, reduces the host spectrum of this M13 to the strains, such as TG1 (supE), which produce an amber suppressor tRNA; it will therefore not be able to replicate in *E. coli* sup+ strains, such as XAC-1.

The 3.8 kb BamHI cassettes, containing the kanamycin-resistance gene of Tn5 and _uidA::pir or pir-116, were respectively purified from M13wm34 and 33 (Metcalf et al., 1994). They were cloned into M13mp10 linearized with BamHI. The recombinant clones were selected by plating on LB+Km agar medium, after electroporating the ligation mixtures into TG1. The conformity of the clones obtained was shown by analysing the restriction profile and by sequencing the region corresponding to the pir-116 mutation.

2) Introduction of the pir or pir-116 Genes into the Genome of *E. coli* XAC-1 by Homologous Recombination The strategy adopted and the various events involved are presented in FIG. 3.

a) First Recombination Event

The XAC-1 strain was transformed by electroporation with 10, 100 or 2000 ng of each RF (mp10-_uidA::pir or pir-116). One-third of each expression mixture was plated out on LB plates containing kanamycin and incubated overnight at 37° C. The mp10-_uidA::pir or pir-116 phages cannot replicate in the strain XAC-1 (sup+). The Km$^R$ marker can therefore only be maintained by integration into the genome of the bacterium via a homologous recombination with the wild-type copy of the gene uida. The results of the electroporations of XAC-1 are presented in Table 1. The transformation efficiency obtained was $4.10^9$ transformants per µg of pUC4K.

TABLE 1

| CONSTRUCT | Number of colonies obtained with the amounts of DNA transformed | | |
|---|---|---|---|
| | 10 ng | 100 ng | 2000 ng |
| M13mp10-_uidA::pir | 1 | 41 | 146 |
| M13mp10-_uidA::pir-116 | 0 | 16 | 124 |

Under the test conditions, the number of integrants increases in a non-linear manner with the amount of DNA. Given the transformation efficiency and the size of the RFs (11.7 kbp), it is possible to have an approximate idea of the level of recombination. By considering the point at 100 ng, a recombination frequency of about $10^{-6}$ is obtained.

b) Second Recombination Event

The second recombination event will then be selected by the resistance of the strains to deoxycholate (Doc$^R$).

To do this, 5 integrants of each construct were cultured in 2XTY medium supplemented with 0.2% sodium deoxycholate. Two distinct populations appeared. Certain clones give quite visible cloudiness after about 8 hours at 37° C. (two clones for the pir construction and three for the pir-116 construction). The other clones gave a dense culture only after one night at 37° C. They were virtually all Km$^S$, as expected. For each of the electroporants studied, 50 Km$^S$ descendants were streaked onto LB medium supplemented with X-Gluc. After 48 hours at 37° C., the UidA$^+$ clones were pale blue whereas those which had undergone an allele replacement (case No. 1, FIG. 3) remained white on this medium (UidA$^-$). Table 2 summarizes the phenotype analysis of the double recombinants obtained.

From 18 to 30% of the double recombinants underwent an allele replacement.

TABLE 2

| Strain | Number of Km$^S$ among the Doc$^R$ | Percentage of UidA among the Km$^S$ |
|---|---|---|
| XAC-1 pir-2 | 50/50 | 18 |
| XAC-1 pir-3 | 50/50 | 24 |
| XAC-1 pir-4 | 50/50 | 34 |
| XAC-1 pir-116-1 | 50/50 | 32 |
| XAC pir-116-4 | 35/50 | 30 |

3) Checking the Pir+ Character Nature of the Strains Obtained by Recombination

In order to ensure the Pir+ character of the strains obtained by double recombination, we transformed three clones of each construct with pBW30 (Metcalf et al., 1994). The fact that transformants were obtained for all the test strains made it possible to show the functionality of the pir and pir-116 genes which were integrated into the genome of XAC-1. Under the same conditions, no transformant is obtained with the parental strain XAC-1. We continued to study 2 XAC-1pir clones (B and C) and 2 XAC-1pir-116 clones (E and D).

4) Checking, by PCR Amplification, of the Strains Obtained by Recombination

In order to confirm the allele replacement, we checked the genomic regions on either side of the uidA locus by PCR amplification. Each pair of oligonucleotides consists of an oligonucleotide corresponding to an internal region of pir and a second oligonucleotide corresponding to a region, close to chromosomal uidA, but not within the fragment which served for the recombination. The sequence of the latter oligonucleotide was determined by means of the ECOUIDAA sequence from Genbank (access number: M14641). We were thus able to verify the exact location of the pir gene in the bacterial genome. The nature of the amplified fragments, whose size is in accordance with that which might be expected, was confirmed by digestion with MluI.

EXAMPLE 2

Construction of Plasmid Vectors Derived from R6K Carrying the Selection Marker sup Phe Vectors were constructed containing ori γ from R6K and the kanamycin-resistance gene (pXL2666). The observation of pXL2666 multimers in the strain BW19610 (pir-116) 5 (Metcalf et al., 1993) led us to study the effect of the cer fragment from ColE1 on this phenomenon. We then introduced the expression cassette of the phenylalanine suppressor tRNA (sup Phe) onto the vector ori γ-Km$^R$-cer (pXL2730). This vector, pXL2760, serves as a basis for the construction of vectors which can be used in gene therapy.

1) Construction and Analysis of Vectors Containing ori γ from R6K and the Kanamycin-resistance Gene a) Constructs In the first plasmid constructed, pXL2666, the kanamycin-resistance gene originates from pUC4K (Vieira and Messing; 1982) and the origin of replication, contained in a 417 bp EcoRI-BamHI fragment, originates from the suicide vector pUT-T7pol (Herrero et al., 1990) (FIG. 4). The transfer of pXL2666 into the strains BW19094 and 19610 (Metcalf et al., 1994) made it possible to show that the amount of plasmid is indeed increased in a pir-116 strain, when compared with the same plasmid in a pir strain. However, the electrophoretic analysis of the undigested plasmids shows that this increase goes hand in hand with the appearance of a few multimeric forms. This phenomenon is quite probably associated with intermolecular recombination between the multiple copies of the plasmid. Thus, we constructed pXL2730 by cloning the cer fragment of the natural E. coli plasmid, ColE1, which had been shown to permit, in cis, the resolution of plasmid dimers (Summers and Sherrat, 1984), into pXL2666. The fragment used corresponds to a 382 bp HPAII fragment from ColE1 (Leung et al., 1985). It contains a specific intermolecular recombination site; in order to function, it involves only host proteins including the recombinases XerC and XerD and the accessory factors ArgR and PepA (Stirling et al., 1988, 1989; Colloms et al., 1990). In order to ensure that the effects observed are indeed due to the cer fragment, we also constructed the control plasmid pXL2754 in which the cer fragment has a 165 bp deletion. This deletion was shown to abolish the action of cer on the resolution of the multimers (Leung et al., 1985). The various cloning steps leading to the construction of these plasmids are presented in FIG. 4.

b) Quantitative and Qualitative Analysis of the Plasmid Species

Analysis by Agarose Gel Electrophoresis

Electrophoretic analysis of the different plasmids constructed allowed the demonstration of various plasmid species, which are variable according to the strains used. The size of the undigested plasmids was evaluated relative to the supercoiled DNA marker. In the pir strain (BW19094), the plasmids pXL2666, 2754 and 2730 are almost entirely in monomeric form. The bands above each main band correspond to various slightly less supercoiled topoisomers, as confirmed by the profile observed after the action of DNA gyrase on pXL2730.

In the case of the pir-116 strain (BW19610), the profiles are different: with the plasmids pXL2666 and 2754 different species are observed ranging from the monomer to multimers (2, 3 or 4 units), the major form being the dimer. After digestion with EcoRI, only the linear plasmid DNA is found; these plasmid species correspond either to plasmid multimers or to various topoisomers. However, since the size of the forms determined according to the supercoiled DNA marker is a whole product of that of the monomer plasmid, it is highly probable that they are multimers. The formation of multimers is most probably attributable to the pir-116 mutation, although the two strains BW19094 and BW19610 are not strictly isogenic (BW19610 is recA). The profile obtained with pXL2730 is different: although multimeric forms are still visible, the major form is the monomeric form. The cer fragment can thus facilitate resolution of the plasmid multimers which we have constructed, independently of recA, in BW19610.

Analysis after Treatment with DNA Topoisomerases

In order to disprove the theory that the forms observed in the strains carrying the pir-116 allele are specific topoisomers, each plasmid preparation was subjected to the action of DNA topoisomerases. The activities of the various enzymes under the experimental conditions are as follows: relaxing of DNA for E. coli DNA topoisomerase I, negative supercoiling of relaxed DNA for E. coli DNA gyrase, and disentanglement of interlaced DNAs and relaxation of supercoiled DNA by S. aureus DNA topoisomerase IV. The action of DNA topoisomerase IV made it possible to show that the high-molecular-weight plasmid forms did not result from the entanglement of several plasmid molecules; in this case, they would then have been converted into the monomeric species. The functionality of the enzyme was, of course, checked on a preparation of kinetoplast DNA, composed of entangled DNA molecules (not shown). The relaxation activity is also visible since species are obtained which migrate less than in the untreated controls. The action of DNA gyrase made it possible to convert the slightly relaxed topoisomers into the more supercoiled species extracted from the bacterium (monomer or dimer mainly). Furthermore, it made it possible to verify that the DNAs prepared are mainly in supercoiled form. The samples thus treated allow the above results to be confirmed as regards the major species for each construct. DNA topoisomerase I did indeed relax DNA, but only partially. This could be due to the fact that the plasmids studied contain only a few single-stranded regions, to which this enzyme preferably binds (Roca, 1995).

2) Introduction of the selection marker sup Phe into pXL2730

We used the expression cassette of the synthetic suppressor tRNA gene (Phe) (Kleina et al., 1990). This introduces a phenylalanine into the growing polypeptide chain in response to a TAG codon. Furthermore, it allows the production in XAC-1 of an ArgE protein which is sufficiently active to allow good growth in arginine-deficient medium. sup Phe is expressed constitutively on the plasmid pCT-2-F (Normanly et al., 1986), from a synthetic promoter derived from the promoter sequence, Plpp, of the E. coli lpp gene. Downstream of this gene, transcription is stopped by the synthetic terminator, $T_{rrnC}$, of the E. coli operon rrnC (Normanly et al., 1986). The various cloning steps are indicated in FIG. 5.

The various subclonings were performed in XAC-1. The functionality of the suppressor tRNA expression cassette is thus checked by means of the β-galactosidase activity of this strain, which only exists if there is suppression of the amber codon of the gene $lacZ_{u118am}$. The final step consists of the introduction of the sup Phe expression cassette into pXL2730. The results obtained with the cer fragment (B-1-b) led us to select this plasmid rather than pXL2666. We retained the kanamycin-resistance gene for ease of subsequent cloning, in particular in order to have available additional screening during the final cloning (loss of $Km^R$).

EXAMPLE 3

Validation of the Plasmid Vector for Applications in Gene Therapy by Transfection of Mouse Fibroblasts 1) Construction of the Reporter Vector pXL2774

In order to test the validity for gene therapy of the system for producting plasmid DNA, we introduced a reporter gene, which can be used in eukaryotic cells, into pXL2760. We used the gene luc coding for *Photinus pyralis* luciferase since the bioluminescence measurement test is very sensitive and is linear over a large range, and the background noise due to the endogenous activity of eukaryotic cells is very low. The luc gene is controlled by promoter-enhancer sequences of a human cytomegalovirus early gene (CMV promoter) which allows a high level of expression. There is an untranslated region at the 3' end of luc, originating from the virus SV40, which contains the polyadenylation signal (poly(A)+). After intermediate cloning which allows the number of available restriction sites to be increased, the "CMV promoter-luc-poly(A)+" cassette is introduced into the minimal vector ori γ-cer-sup Phe (pXL2760) in place of the $Km^R$ marker. The resulting plasmid has been named pXL2774. FIG. 6 collates the various cloning steps. The ligation mixtures were transformed into XAC-1pir-116 by electroporation. Incubation allowing the bacteria to express selection markers is carried out in rich medium (SOC medium); it was thus necessary to wash the cells twice with M9 medium before plating out. This made it possible to remove the residual medium which would have resulted in culture background noise on minimal medium.

The medium chosen to plate out the electroporated cells is M9 minimal medium, which makes it possible to select bacteria expressing a suppressor tRNA and thus the presence of our plasmids. The addition of X-Gal makes it possible, by means of the blue colouration, to visualize the expression of the suppressor LRNA. The dishes are analysed after about 20 hours at 37° C. The absence of colonies on the DNA-free control assures us that the selection is correct, even with dense seedings. All the clones examined by restriction (8) do indeed carry a plasmid, corresponding to the expected profile. The plasmid thus constructed, pXL2774, was prepared from a clone cultured in one liter of liquid M9 medium (about 18 hours at 37° C.), by a technique involving, inter alia, an ion-exchange (Promega kit, MegaPreps). The amount of DNA collected is 2 mg.

2) Analysis of the Reporter Vector pXL2774 Transfected into Mammalian Cells

The capacity of pXL2774 to transfect eukaryotic cells and to allow the expression of luciferase is evaluated by transfection into NIH 3T3 mouse fibroblasts. The vector chosen as reference is the plasmid pXL2622 (this is the plasmid pGL2 from Promega whose SV40 promoter has been replaced by the CMV promoter) which carries the same luciferase expression cassette as pXL2774, but on a different replicon. This is a 6.2 kb ColE1 derivative which carries the ampicillin-resistance gene. This plasmid serves as a control. The luciferase activities (expressed as RLU, or relative luminescence units) are indicated in Table 3.

The best results were obtained with a "lipofectant charges/DNA charges" ratio of 6; under these conditions, pXL2622 and 2774 appear to be equivalent.

TABLE 3

| | pXL2622 | | | pXL2774 | | |
|---|---|---|---|---|---|---|
| Charge ratios | RLU/µg of proteins and per well | Average | Coefficient of variation (%) | RLU/µg of proteins and per well | Average | Coefficient of variation (%) |
| 0 | 0.0 0.0 0.0 | not detectable | | 0.0 0.0 0.0 | not detectable | |
| 3 | 9.9 $10^6$ 6.2 $10^6$ 6.6 $10^6$ | 7.6 $10^6$ | 22 | 3.3 $10^6$ 2.9 $10^6$ 2.4 $10^6$ | 2.9 $10^6$ | 13 |
| 6 | 1.2 $10^6$ 1.5 $10^7$ 1.9 $10^7$ | 1.5 $10^7$ | 19 | 9.4 $10^6$ 9.9 $10^6$ 1.1 $10^7$ | 1.0 $10^7$ | 7 |
| 9 | 9.5 $10^6$ 7.5 $10^6$ 1.4 $10^7$ | 1.0 $10^7$ | 26 | 1.1 $10^7$ 8.3 $10^6$ 8.5 $10^6$ | 6.4 $10^6$ | 13 |

EXAMPLE 4

Verification of the Suicide Vector Nature in *E. coli* of the pCOR Plasmids

The non-replicative nature of the pCOR-type plasmids derived from R6K was verified by an electroporation experiment in JM109 *E. coli* (Yanisch-Perron et al., 1985) of the plasmids pUC4K (ori ColEI-KmR, (Vieira and Messing, 1982)) and pXL2730 (ori gamma from R6K-KmR, see Example 2). The electroporator used is the Biorad Gene Pulser and the electrocompetent JM109 cells are prepared and used according to the manufacturer's procedure (Bacterial electro-transformation and pulse controller instruction manual. catalog number 165-2098).

The electrotransformed cells were plated out on LB medium supplemented with kanamycin (50 mg/l) and incubated overnight at 37° C. The results obtained are presented below.

| | Results | | |
|---|---|---|---|
| Plasmid | Amount transformed (ng) | Number of transformants | Efficacy (number of transformants/ng of plasmid) |
| pUC4K | 0.01 | >>2000 | >$2 10^5$ |
| pXL2730 | 5 | 0 | 0 |

These results show that there is a minimum of 5 log of difference between the efficacy of transformation of a ColEI derivative (pUC4K) and that of an R6K derivative (pXL2730) in a strain which does not express the pir gene. In a pir+ strain such as XAC-1pir-116, the electrotransformation efficacy of R6K-derived plasmids conventionally reaches or exceeds the $10^8$ transformants/µg of plasmid.

EXAMPLE 5

Production of Plasmid DNA by High-density Culturing of the *E. coli* Strain XAC-1pir-116 (pXL2774): Fermentation Process 5.1. Strains: Production in XAC-1pir-116 *E. coli* (Example 1) of a minimal plasmid, pXL2774; this plasmid comprises the following elements: ori R6K-cer-tRNAamsupPhe and an expression cassette of the luc reporter gene under the control of the CMV promoter (Example 3). A high-productivity process for the production of plasmids of this type was developed.

5.2. Culturing Media and Conditions:

a) Growth Medium:

Composition of the medium defined used for the inoculum cultures (g/l): $Na_2HPO_4$ 6, $KH_2PO_4$ 3, NaCl 0.5, $NH_4Cl$ 1, $NH_4H_2PO_4$ 3, glucose 5, $MgSO_4.7H_2O$ 0.24, $CaCl_2.2H_2O$ 0.015, thiamine HCl 0.010

Composition of the complex medium used for the fed-batch cultures (g/l): $KH_2PO_4$ 8, $K_2HPO_4$ 6.3, $Na_2HPO_4$ 1.7, $(NH_4)_2SO_4$ 0.74, $NH_4Cl$ 0.12, yeast extract 3, glucose 2, $MgSO_4.7H_2O$ 2.4 g/l, $CaCl_2.2H_2O$ 0.015, thiamine 0.010, solution of salts (Fe, Mn, Co, Zn, Mo, Cu, B, Al).

Composition of the medium defined for the cultures in fed-batch medium identical to the complex medium but the yeast extract is replaced by 2.5 g/l of $NH_4Cl$.

b) Conditions of fed-batch culturing:

Studies in 2-liter fermenters (Setric France) containing 1 l of medium were carried out in order to define the optimum conditions for growing and producing plasmid DNA. The fermenter was inoculated with 80 ml of an inoculum culture arrived at the start of the stationary phase of growth.

During the fermentation, the pH was controlled and adjusted automatically between 6.9 and 7.0 with 10% (w/v) aqueous ammonia; the temperature is maintained at 37° C.; the aeration was set at 75 l/h ((1.1 vvm) at a pressure of 0.2 bar and the dissolved oxygen was adjusted to (40% of air saturation by retroaction on the stirring rate and, if necessary, by enrichment with pure oxygen.

All the parameters (pH, temperature, stirring, OD, $O_2$ and $CO_2$ in the effluent gases) were collected and calculated in line via an HP3852 interface connected to a Hewlett-Packard 9000.

The base composition of the supply medium is as follows: 50% carbon source, 0.7% magnesium sulphate, 0.02% thiamine; for the complex medium, yeast extract was added to a concentration preferably of between 5 and 10%.

In order to adapt the culture conditions to 800-liter fermenters, production sequences composed of two successive inoculum cultures were carried out, on a laboratory scale: inoculum I in an agitated conical flask and inoculum II in a 2-liter fermenter (batch culturing), followed by fed-batch production culturing, in a 7-liter fermenter.

5.3. Results

Various culture conditions were studied in complex medium, in defined medium, and at various growth rates. In all cases, after initial batch culturing of the bacterial strain and consumption of the carbon source, the supply medium was added to the fermenter by means of a peristaltic pump coupled to a pre-programned addition profile. This profile was deduced from previous experiments in which the supply rate had been controlled either by the level of dissolved oxygen or by a constant growth rate.

Furthermore, in order to extrapolate without difficulty the 2-liter fermentation condition to an 800 l fermenter without overoxygenation of the medium, the maximum oxygen demand at the end of the culturing was set at 2.5–3 mM/min. For this, the growth rate of the microorganism was reduced, if necessary, by varying the supply rate of the complementary charge.

As seen in Table 4, very good results were obtained both in complex medium and in defined medium, both on the laboratory scale and on the 800-liter fermenter scale; furthermore, the plasmid DNA growth and production kinetics are entirely comparable (cf. FIGS. 6 and 7).

TABLE 4

|  | Complex medium | | Defined medium |
| --- | --- | --- | --- |
|  | 2 or 7 l fermenter | 800 l fermenter | 2 l fermenter |
| Duration of fermentation (hours) | 40 | 39 | 48 |
| µ h-1 | 0.130 | 0.132 | 0.124 |
| OD (600 nm) | 114 | 100 | 94 |
| X g/l | 44 | 37 | 30 |
| Plasmid DNA (mg/l medium) | 115 | 100 | 100 |
| Plasmid DNA (mg/gX) | 2.6 | 2.7 | 3.3 |

X = Biomass (weight of dry cells)

From the overall results it emerges that:

changing the scale of the fermenter from 2 liters to 800 liters can be carried out without any problem, the oxygen consumed is strongly correlated to the biomass produced (1.08 g $O_2$/g of biomass produced), the plasmid is stable for at least 50 generations without selection pressure, a high biomass, greater than 40 g of dry cells/liter, can be obtained in complex medium, the plasmid DNA production reaches 100 mg of supercoiled DNA/l of medium, there is very good correlation between the DNA production and the biomass: the production can be estimated to (1 mg of plasmid DNA/OD unit, or alternatively (2.7 mg of plasmid DNA/g of biomass, irrespective of the duration of fermentation, the use of a defined medium also makes it possible to achieve a high biomass (30 g of dry cells/l) and high plasmid DNA production (100 mg/l), without any loss of productivity.

EXAMPLE 6

Transfer of pXL2774 into animal cells, in vitro and in vivo 6.1. in vitro Transfer of PXL2774 into Animal Cells The capacity of the minimal plasmid pXL2774 to transfect various cell lines was tested in vitro, on cells of both human origin and murine origin. The pXL2784 plasmid was used as control. It contains the same eukaryotic expression cassette (CMV promoter-luciferase-polyA) as pXL2774, but this is a 6.4 kb ColE1 derivative which comprises the gene for imparting kanamycin resistance in E. coli.

The cells tested are the following:

| Cells | Type | Atcc ref./ literature ref. |
| --- | --- | --- |
| 3LL | Mouse pulmonary carcinoma | |
| NIH 3T3 | Mouse embryo fibroblasts | CCL92 |
| 293 | Human embryo renal cells transformed with type-5 adenovirus | CRL1573 |

-continued

| Cells | Type | Atcc ref./ literature ref. |
| --- | --- | --- |
| HeLa | Human carcinoma from the neck of the womb | CCL2 |
| Caco-2 | Human colon adenocarcinoma | HTB37 |
| H460 | Human lung carcinoma with no small cells | HTB177 |
| ECV 304 | Human umbilical cord endothelial cells | Takahashi et al., 1990 |

The transfection conditions were as follows:

D-1: Inoculation of the cells at a density of 100,000 cells per 2 $cm^2$ well (24-well plate) in DMEM medium (Dulbecco's modified Eagle Medium) supplemented with 10% foetal calf serum (FCS).

D-3: Transfection of the cells, by 10 µl of a transfection solution containing: 0.5 µg of DNA, 150 mM NaCl, 5% glucose and 3 nmol of RPR120 535 lipofectant per µg of DNA, in 250 µl of culture medium, which is or is not supplemented with 10% FCS. After incubation for 2 hours, the medium is replaced by 500 µl of DMEM medium supplemented with 10% FCS.

D-4: Renewal of the culture medium

D-5: Washing of the cells with PBS, followed by lysis with 100 µl of Promega lysis buffer (Promega Cell Lysis Buffer E153 A). Assay of the luciferase activity is carried out in a Lumat LB 9501 luminometer (Berthold) on 10 µl of lysate, with a 10-second duration of integration. The reactant used is that from Promega (Promega Luciferase Assay Substrate). The results, collated in the following tables, are expressed in RLU (Relative Lights Units) for 10 µl of lysate (average of measurement on 4 wells). The coefficients of variation (CV) are also given.

The results of transfections in the absence of serum are presented below.

|  | CELL TYPES | | |
| --- | --- | --- | --- |
|  | NIH 3T3 | 3LL | 293 |
| pXL2774 | 37 763 380 | 559 270 | 1 884 200 RLU |
|  | 16 | 25 | 73 CV |
| pXL2784 |  | 113 764 | 1 723 546 RLU |
|  |  | 24 | 101 CV |

|  | CELL TYPES | | | |
| --- | --- | --- | --- | --- |
|  | HeLa | CaCo2 | H460 | ECV304 |
| pXL2774 | 11 000 000 | 1 108 422 | 1 459 501 | 36 450 |
|  | 15 | 14 | 5 | 23 |
| pXL2784 | 557 930 | 93 610 | 7 563 | 168 795 |
|  | 87 | 40 | 11 | 40 |

The results of transfections in the presence of serum (10%) are presented below:

| | CELL TYPES | | |
|---|---|---|---|
| | NIH 3T3 | 3LL | 293 |
| pXL2774 | 50 612 590 12 | 566 377 18 | 992 500 59 |
| PXL2784 | 12 693 780 38 | 436 704 12 | 2 300 000 47 |

| | CELL TYPES | | |
|---|---|---|---|
| | HeLa | H460 | ECV304 |
| pXL2774 | 9 490 000 25 | 857 385 16 | 18 021 30 |
| PXL2784 | 1 508 480 23 | 433 023 27 | 32 074 47 |

These results reveal the capacity of pXL2774 to transfect effectively, in vitro, various cell types of both murine and human origin. The expression of the luc reporter gene makes it possible to show that its transfection efficacy is at least as good as that of a "standard" plasmid, derived from ColE1, which carries the same expression cassette of luciferase.

6.2. in vivo Transfer, in Animals (Mice), of pXL2774 a) Model 1: Naked DNA in mouse Cranial Tibial Muscle

Naked plasmid DNA, dissolved in "5% glucose, 150 mM NaCl" is injected into the cranial tibial muscle of OF1 mice. The muscles are removed 7 days after injection, chopped up, homogenized in 750 μl of lysis buffer (Promega Cell Lysis Buffer E153A) and then centrifuged at 20,000×g for 10 minutes.

Assay of the luciferase activity is carried out on 10 μl of supernatant after addition of 50 μl of reagent (Promega Luciferase Assay Substrate). The reading is carried out on a Lumat LB9501 luminometer (Berthold) with a 10-second duration of integration.

The results are presented in the table below.

| Plasmid | pXL2784 | pXL2774 | pXL2784 | pXL2774 |
|---|---|---|---|---|
| Number of muscles: | 8 | 8 | 10 | 10 |
| Volume injected (μl): | 30 | 30 | 33 | 33 |
| (μg of DNA/muscle | 19 | 13.5 | 10 | 6.25 |
| RLU (for 10 μl) | | | | |
| Average | 80 922 | 471 733 | 35329 | 30569 |
| Standard deviation | 104 573 | 402 602 | 37041 | 35774 |

These results show that a conditional replication plasmid such as pXL2774 is indeed capable of transfecting mouse muscle cells in vivo and of doing so with comparable, or even superior, efficacy to that of a "standard" plasmid, derived from ColE1, which carries the same expression cassette of the luciferase gene.

b) Model 2: 3T3 HER2 tumour model

The model is as follows:

Swiss/nude adult female type mice

Experimental tumours induced after injection of 107 3T3 HER2 cells subcutaneously into the flank.

The transfection mixture is injected 7 days after injection of the cells.

Solutions injected: The DNA is first dissolved in the buffer. After addition of all the products, the mixture contains, besides the DNA, NaCl (150 mM) and 5% D-glucose in water or 5 mM HEPES buffer.

Two days after the injection, the tumour tissue is removed, weighed and then chopped up and homogenized in 750 μl of lysis buffer (Promega Cell Lysis Buffer E153 A). After centrifugation (20,000×g for 10 minutes), 10 μl of supernatant are removed and allow the luciferase activity to be evaluated. This activity is determined by measuring the total light emission obtained after mixing with 50 μl of reagent (Promega Luciferase Assay Substrate) in a Lumat LB 9501 luminometer (Berthold) with a 10-second duration of integration.

The resulting activity is expressed in RLU (Relative Light Units) estimated in the entire tumour lysis supernatant.

| | | Results: | | | | |
|---|---|---|---|---|---|---|
| | Plasmid | | | | | |
| Buffer | | | [DNA] | RLU/tumour results | | |
| H2O or HEPES | reference | μg/tumour | final in inj. sol. | average | standard deviation | +/n |
| HEPES | pXL2784 | 10 | 0.5 μg/μl | 744 150 | 682 434 | 6/6 |
| | pXL2774 | 10 | 0.5 μg/μl | 1 016 380 | 1 322 500 | 5/6 |
| H2O | pXL2784 | 24 | 0.6 μg/μl | 2 906 073 | 1 745 857 | 8/8 |
| | pXL2774 | 16.8 | 0.4 μg/μl | 4 292 043 | 4 995 187 | 6/6 |
| H2O | pXL2784 | 7.5 | 0.3 μg/μl | 702 554 | 552 207 | 6/7 |
| | pXL2774 | 5 | 0.2 μg/μl | 3 413 430 | 4 000 875 | 6/6 |

These results show that a conditional replication plasmid, such as pXL2774, is indeed capable of transfecting mouse tumour cells in vivo and of doing so with an efficacy at least comparable to that of a "standard" plasmid, derived from ColE1, which carries the same expression cassette of the luciferase gene.

These various experiments made it possible to demonstrate that the conditional replication plasmids, and more particularly pXL2774, did indeed have animal cell transfection characteristics that are essential for use in gene therapy. More precisely, the following were shown:

1) the capacity of pXL2774 to transfect efficiently, in vitro, various cell types, of human or murine origin;

2) the capacity of pXL2774 to transfect, in vivo, mouse muscle;

3) the capacity of pXL2774 to transfect, in vivo, tumour cells implanted into mice.

The electrotransformation, fermentation and transfection experiments thus made it possible to validate conditional replication plasmids as vectors which can be used in gene therapy by showing i) that they did not replicate detectably in an *E. coli* strain which does not express the pir gene (conditional origin of replication)

ii) that they could be produced on a scale compatible with industrial production, in a medium which can be totally defined and which does not contain antibiotics;

iii) that these plasmids could transfect, in vitro and especially in vivo, mammalian cells.

EXAMPLE 7 in vitro Production of Recombinant Proteins 7.1. Construction of the Expression Vector In order to show the feasibility of such an approach, we constructed an expression vector according to the criteria described above (Examples 2 and 3). This vector, pXL3056, contains:

1) the bacterial part which comprises the conditional origin of replication (ori gamma), the cer fragment of ColE1 and the gene which ensures selection in bacteria (sup)

2) the expression cassette, based on the system described by Studier (Studier et al., 1990), comprises the promoter of gene 10 of bacteriophage T7, the lacO operator, the gene coding for aFGF 154 (acidic Fibroblast Growth factor, form containing 154 amino acids) (Jaye et al., 1986), the TF terminator of bacteriophage T7. This expression cassette is identical to the one present on the pXL2434 plasmid described in application WO 96/08572.

The construction of pXL3056 is presented in FIG. 8. The EcoRI-BglII fragment of pXL2434 (1.1 kb) containing the aFGF expression cassette is cloned in the pXL2979 conditional replication vector (1.1 kb purified fragment) at the BglII and EcoRI sites in order to generate pXL3056.

pXL2979 results from the ligation of 3 fragments: i) AccI-XbaI fragment of pXL2730 (0.8 kb, which provides ori gamma and cer), ii) NarI-SalI fragment of pXL2755 (0.18 kb, which provides the sup Phe gene), iii) SalI-SpeI fragment of pXL2660 (1.5 kb, which provides the kanamycin-resistance gene).

pXL2660 results from the cloning of the 1.2 kb PstI fragment of pUC4K (Vieira and Messing, 1982) in pMTL22 (Chambers et al., 1988) linearized with PstI.

7.2. Production of the Expression Strain

The plasmid pXL3056 is introduced by transformation into the XAC-1pir-116 strain. The resulting strain is then transformed by the plasmid PT7pol23 (Mertens et al., 1995), at 30° C. In order to express the gene of interest under control of the T7 promoter, the bacterium must contain, in its genome, on a plasmid or a bacteriophage, a cassette to allow the expression of the RNA polymerase of bacteriophage T7. In the example described, we used the plasmid PT7pol23, which is compatible with R6K derivatives such as pXL3056, and which allows the temperature-inducible expression of bacteriophage T7 RNA polymerase. However, it can also be envisaged to lysogenize the XAC-1pir-116 strain with lambda DE3 (Studier et al., 1990) in order to conserve only one plasmid and to induce the production of T7 RNA polymerase by IPTG rather than by temperature.

7.3. Expression of aFGF

The XAC-1pir-116 strain (pXL3056+PT7pol23) is cultured at 30° C., in M9 minimum medium supplemented with 0.2% of casamino acids (DIFCO) and kanamycin (25 µg/ml), up to an optical density at 600 nm of 0.6–1. Half of the culture is then placed at 42° C. (induction of the T7 RNA polymerase), while the other half remains at 30° C. (negative control). The same experiment is carried out with the XAC-1pir-116 (pXL3056+pUC4K) strain which constitutes a control for the expression of aFGF in the absence of T7 RNA polymerase.

The results obtained are presented in FIG. 9. They show that the production of aFGF is comparable or superior to that observed with BL21(DE3)(pXL2434) (WO 96/08572), which clearly shows the potential of conditional replication plasmids for the expression of recombinant proteins in vitro, especially in *E. coli*.

EXAMPLE 8

Construction of a pCOR Vector which Expresses a Wild-type or Hybrid p53 Protein.

This example describes the construction of conditional replication vectors according to the invention containing a nucleic acid which codes for a p53 protein. These vectors can be used to restore a p53-type activity in deficient (mutated, deleted) cells such as, in particular, tumour cells.

The eukaryotic expression cassette contains the following elements:

1) CMV "immediate early" promoter (positions −522 to +72) followed by the leader sequence of the thymidine kinase gene of type I herpes simplex virus (position −60 to +1 of the gene, with reference to the sequence in the article by McKnight, S.†L. (1980) Nucleic Acids Res. 8:5949–5964);

2) a nucleic acid which codes for wild-type p53 protein or for a p53 variant, as described in application PCT/FR 96/01111 (V325K variant=V325 with a Kozak sequence with ATG);

3) the polyA polyadenylation sequence of SV40.

These elements were placed in the form of a fragment AscI-XbaI on the pCOR vector pXL2988 between the sites BssHII and SpeI. pXL2988 is identical to pXL2979 (Example 7.1.) apart from the presence of an additional element, a sequence capable of forming a DNA triple helix composed of 17 times the trinucleotide GAA, placed alongside the gamma origin of replication.

The resulting plasmids are named pXL3029 and 3030 (FIG. 10).

The functionality of these constructions was verified in vitro on p53-SAOS2 cells in culture by measuring the transcriptional-activator activity of p53 or p53superWT.

Bibliography

Alting-Mees, M. A., J. A. Sorge, and J. M. Short. 1992. Methods Enzymol. 216:483–495

Blum, P., D. Holzschu, H. S. Kwan, D. Riggs, and S. Artz. 1989. J. Bacteriol. 171:538–546.

Brosius, J. 1989. Methods Enzymol. 216:469–483.

Chambers, S. P., S. E. Prior, D. A. Barstow, and N. P. Minton. 1988. Gene 68:139–149.

Chung, C. T., and R. H. Miller. 1988. Nucleic Acids Res. 16:3580.

Colloms, S. D., P. Sykora, G. Szatmari, and D. J. Sherrat. 1990 J. Bacteriol. 172:6973–6980.

Datta, N., and P. Kontomichalou. 1965. Nature 208:239–241.

Dickely, F., D. Nilsson, E. B. Hansen, and E. Johansen. 1995. Mol. Microbiol. 15:839–847.

Filutowicz, M., S. Dellis, I. Levchenko, M. Urh, F. Wu, and D. York. 1994. Prog. in Nucleic Acid Res. and Mol. Biol. 48:239–273.

Gibson, T. J. 1984. Ph.D Thesis. University of Cambridge.

Greener, A., M. Filutowicz, M. McEachern, and D. Helsinki. 1990. Mol. Gen. Genet. 224:24–32.

Herrero, M., V. de Lorenzo, and K. N. Timmis. 1990. J. Bacteriol. 172:6557–6567.

Hodgson, C. P. 1995. Bio/Technology 13:222–225.

Inuzuka, M., and Y. Wada. 1985. EMBO J. 4:2301–2307.

Jaye, M. et al., (1986) Science 233:541–5

Kleina, L. G., J. M. Masson, J. Normanly, J. Abelson, and J. H. Miller. 1990. J. Mol. Biol. 213:705–717.

Kowalczykowski, S. C., and A. K. Eggleston. 1994. Annu. Rev. Biochem. 63:9991–10043.

Leung, D. W., E. Chen, G. Cachianes, and D. V. Goeddel. 1985. DNA 4:351–355.

Maniatis, T., E. F. Fritsch, and J. Sambrook. 1989. Cold Spring Harbor Laboratory, Cold Spring Harbor, N.Y.

Meinnel, T., E. Schmitt, Y. Mechulam, and S. Blanquet. 1992. J. Bacteriol. 174:2323–2331.

Mertens, N., E. Remant and W. Fiers. (1995) Bio/Technology 13:175–179

Messing, J., and J. Vieira. 1982. Gene 19: 269–276.

Metcalf, W. W., W. Jiang, and B. L. Wanner. 1994. Gene 138:1–7.

Miller, V. L., and J. J. Mekalanos. 1988. J. Bacteriol. 170:2575–2583.

Normanly, J., J. M. Masson, L. G. Kleina, J. Abelson, and J. H. Miller. 1986. Proc. Natl. Acad. Sci. USA 83:6548–6552.

Normanly, J., L. G. Kleina, J. M. Masson, J. Abelson, and J. H. Miller. 1990. J. Mol. Biol. 213:719–726.

Roca, J. 1995. TIBS 20:156–160.

Saïki, R. K., S. Scharf, F. Faloona, K. B. Mullis, G. T. Horn, H. A. Erlich, and N. Arnheim. 1985. Science 230:1350–1354.

Sanger, F., S. Nicklen, and A. R. Coulson. 1977. Proc. Natl. Acad. Sci. USA 74:5463–5467.

Sawadogo, M., and M. W. Van Dyke. 1991. Nucleic Acids Res. 19:674.

Scott, J. R. 1984. Microbiol. Rev. 48:1–23.

Simoes, D. A., M. Dal Jensen, E. Dreveton, M. O. Loret, S. Blanchin-Roland, J. L. Uribelarrea, and J. M. Masson. 1991. Ann. N.Y. Acad. Sci. 646:254–258.

Simon, R., U. Priefer, and A. Pühler. 1983. Bio/Technology 1:784–791.

Sinha, N. D., J. Biernat, J. McManus, and H. Köster. 1984. Nucleic Acids Res. 12:4539–4557.

Stirling, C. J. G. Stewart, and D. J. Sherrat. 1988. Mol. Gen. Genet. 214:80–84.

Stirling, C. J., S. D. Colloms, J. F. Collins, G. Szatmari, and D. J. Sherrat. 1989. EMBO J. 8:1623–1627.

Studier, F. W., A. H. Rosenberg., J. J. Dunn and J. W. Dubendorff (1990). Methods Enzymol 185:60–89.

Summers, D. K., and D. J. Sherrat. 1984. Cell 36:1097–1103.

Takahashi, K., Y. Sawasaki, J. Hata, K. Mukai and T. Goto. (1990) In Vitro Cell Dev. Biol. 26:265–74.

Vieira, J., and J. Messing. 1982. Gene 19:259–268.

Wiechelman, K., R. Braun, and J. Fitzpatrick. 1988. Anal. Biochem. 175:231–237.

Yanisch-Perron, C. Vieira and J. Messing (1985) Gene 33:103–119 13.

---

What is claimed is:

1. An extrachromosomal DNA molecule comprising a heterologous gene encoding a protein and a conditional origin of replication whose functionality in a prokaryotic host cell requires a replication initiating protein specific for said origin of replication and foreign to the prokaryotic host cell, a suppressor transfer tRNA for an amber codon, and a cer fragment from ColE1, wherein said DNA molecule does not encode the replication initiating protein.

2. The extrachromosomal DNA molecule according to claim 1, wherein the heterologous gene encodes acidic fibroblast growth factor.

3. The extrachromosomal DNA molecule according to claim 2, wherein the heterologous gene is under the control of a bacteriophage T7 promoter.

4. A prokaryotic recombinant host cell comprising a heterologous replication initiating protein that activates a conditional origin of replication and an extrachromosomal DNA molecule comprising a heterologous gene encoding a protein, a selection gene encoding a suppressor transfer RNA for a specific codon, and a conditional origin of replication whose functionality in the prokaryotic recombinant host cell requires a replication initiating protein specific for said origin of replication and foreign to the host cell, wherein said DNA molecule does not encode the replication initiating protein.

5. A method for producing an extrachromosomal DNA molecule comprising a heterologous gene encoding a protein, a selection gene encoding a suppressor transfer RNA for a specific codon, and a conditional origin of replication whose functionality in a prokaryotic host cell requires a replication initiating protein specific for said origin of replication and foreign to the host cell, wherein said DNA molecule does not encode the replication initiating protein, comprising:
    a) culturing a prokaryotic recombinant host cell according to claim 4; and
    b) isolating the extrachromosomal DNA molecule produced by the host cell.

6. The method according to claim 5, wherein the prokaryotic recombinant host cell is *Escherichia coli*.

7. The method according to claim 5, wherein the conditional origin of replication originates from a bacterial plasmid or a bacteriophage.

8. The method according to claim 7, wherein the bacterial plasmid or the bacteriophage is selected from the group consisting of RK2, R6K, R1, pSC101, Rtsl, F, RSF1010, P1, P4, lambda, Phi82 and Phi80.

9. The method according to claim 7, wherein the bacterial plasmid is R6K.

10. The method according to claim 9, wherein the conditional origin of replication comprises SEQ ID No. 1.

11. The method according to claim 5, wherein the prokaryotic recombinant host cell expresses a π initiator protein.

12. The method according to claim 11, wherein the π initiator protein is encoded by gene pir-116.

13. The method according to claim 11, wherein the π initiator protein is encoded by SEQ ID No. 2.

14. The method according to claim 5, wherein the selection gene is a suppressor of an amber transfer RNA, and the host cell contains a gene essential under certain culture conditions comprising an amber mutation.

15. The method according to claim 5, wherein the extrachromosomal DNA molecule further comprises a target region for a site-specific recombinase.

16. The method according to claim 15, wherein the target region for the site-specific recombinase is a cer fragment from ColE1.

17. The method according to claim 5, wherein the extrachromosomal DNA molecule is pXL2774.

18. The prokaryotic recombinant host cell according to claim 4, wherein the cell is *Escherichia coli*.

19. The prokaryotic recombinant host cell according to claim 4, wherein the conditional origin of replication is from a bacterial plasmid or a bacteriophage.

20. The prokaryotic recombinant host cell according to claim 19, wherein the conditional origin of replication is from a bacterial plasmid or a bacteriophage selected from the group consisting of RK2, R6K, R1, pSC101, Rtsl, F, RSF1010, P1, P4, lambda, Phi82 and Phi80.

21. The prokaryotic recombinant host cell according to claim 19, wherein the conditional origin of replication is from bacterial plasmid R6K.

22. The prokaryotic recombinant host cell according to claim 4, wherein the host cell expresses a π initiator protein.

23. The prokaryotic recombinant host cell according to claim 22, wherein the π initiator protein is encoded by gene pir-116.

24. The prokaryotic recombinant host cell according to claim 22, wherein the π initiator protein is encoded by SEQ ID No.: 2.

25. The prokaryotic recombinant host cell according to claim 4, wherein the host cell further comprises a gene comprising an amber mutation, wherein said gene is essential under certain culture conditions.

26. The extrachromosomal DNA molecule of claim 2, wherein the heterologous gene is under the control of a CMV promoter.

27. The extrachromosomal DNA molecule of claim 3, which is designated pXL3056.

28. An extrachromosomal DNA molecule comprising:
    a gene encoding acidic fibroblast growth factor operably linked to a cytomegalovirus (CMV) promoter and an SV40 polyadenylation sequence;

a conditional origin of replication from plasmid R6K whose functionality in a prokaryotic host cell requires a replication initiating protein specific for said origin of replication and foreign to the prokaryotic host cell;

a cer fragment; and a phenylalanine suppressor tRNA gene;

wherein the extrachromosomal DNA molecule does not contain a gene encoding the replication initiating protein foreign to the prokaryotic host.

29. An extrachromosomal DNA molecule comprising a heterologous gene encoding acidic fibroblast growth factor and a conditional origin of replication whose functionality in a prokaryotic host cell requires a replication initiating protein specific for said origin of replication and foreign to the prokaryotic host cell, wherein said DNA molecule does not encode the replication initiating protein.

30. The extrachromosomal DNA molecule according to claim 29, wherein the conditional origin of replication originates from a bacterial plasmid or a bacteriophage.

31. The extrachromosomal DNA molecule according to claim 30, wherein the bacterial plasmid or the bacteriophage is selected from the group consisting of RK2, R6K, R1, pSC101, Rtsl, F, RSF1010, P1, P4, lambda, Phi82 and Phi80.

32. The extrachromosomal DNA molecule according to claim 30, wherein the bacterial plasmid is R6K.

33. The extrachromosomal DNA molecule according to claim 32, wherein the conditional origin of replication comprises the gamma origin of replication of plasmid R6K.

34. The extrachromosomal DNA molecule according to claim 33, wherein the conditional origin of replication comprises SEQ ID No: 1.

35. The extrachromosomal DNA molecule according to claim 29, further comprising a selection gene, wherein the selection gene does not impart resistance to an antibiotic.

36. The extrachromosomal DNA molecule according to claim 35, wherein the selection gene encodes a suppressor transfer RNA for a specific codon.

37. The extrachromosomal DNA molecule according to claim 36, wherein the suppressor is a suppressor transfer tRNA for an amber codon.

38. The extrachromosomal DNA molecule according to claim 29, further comprising a target region for a site-specific recombinase.

39. The extrachromosomal DNA molecule according to claim 38, wherein the target region for the site-specific recombinase is a cer fragment from ColE1.

40. The extrachromosomal DNA molecule according to claim 29, wherein the heterologous gene is under the control of a bacteriophage T7 promoter.

41. A prokaryotic recombinant host cell comprising a heterologous replication initiating protein that activates a conditional origin of replication and an extrachromosomal DNA molecule comprising a heterologous gene encoding acidic fibroblast growth factor and a conditional origin of replication whose functionality in the prokaryotic recombinant host cell requires a replication initiating protein specific for said origin of replication and foreign to the host cell, wherein said DNA molecule does not encode the replication initiating protein.

42. The prokaryotic recombinant host cell according to wherein the cell is *Escherichia coli.*

43. The prokaryotic recombinant host cell according to claim 41, wherein the conditional origin of replication is from a bacterial plasmid or a bacteriophage.

44. The prokaryotic recombinant host cell according to claim 43, wherein the conditional origin of replication is from a bacterial plasmid or a bacteriophage selected from the group consisting of RK2, R6K, R1, pSC101, Rtsl, F, RSF1010, P1, P4, lambda, Phi82 and Phi80.

45. The prokaryotic recombinant host cell according to claim 43, wherein the conditional origin of replication is from bacterial plasmid R6K.

46. The prokaryotic recombinant host cell according to claim 41, wherein the host cell expresses a $\pi$ initiator protein.

47. The prokaryotic recombinant host cell according to claim 46, wherein the $\pi$ initiator protein is encoded by gene pir-116.

48. The prokaryotic recombinant host cell according to claim 46, wherein the $\pi$ initiator protein is encoded by SEQ ID No.: 2.

49. The prokaryotic recombinant host cell according to claim 41, wherein the host cell further comprises a gene comprising an amber mutation, wherein said gene is essential under certain culture conditions.

50. A method for producing an extrachromosomal DNA molecule comprising a heterologous gene encoding acidic fibroblast growth factor and a conditional origin of replication whose functionality in a prokaryotic host cell requires a replication initiating protein specific for said origin of replication and foreign to the host cell, wherein said DNA molecule does not encode the replication initiating protein, comprising:

a) culturing a prokaryotic recombinant host cell according to claim 41; and b) isolating the extrachromosomal DNA molecule produced by the host cell.

51. The method according to claim 50, wherein the prokaryotic recombinant host cell is *Escherichia coli.*

52. The method according to claim 50, wherein the conditional origin of replication originates from a bacterial plasmid or a bacteriophage.

53. The method according to claim 52, wherein the bacterial plasmid or the bacteriophage is selected from the group consisting of RK2, R6K, R1, pSC101, Rtsl, F, RSF1010, P1, P4, lambda, Phi82 and Phi80.

54. The method according to claim 53, wherein the bacterial plasmid is R6K.

55. The method according to claim 54, wherein the conditional origin of replication comprises SEQ ID No. 1.

56. The method according to claim 50, wherein the prokaryotic recombinant host cell expresses a $\pi$ initiator protein.

57. The method according to claim 56, wherein the $\pi$ initiator protein is encoded by gene pir-116.

58. The method according to claim 56, wherein the $\pi$ initiator protein is encoded by SEQ ID No. 2.

59. The method according to claim 50, wherein the extrachromosomal DNA molecule further comprises a selection gene encoding a suppressor transfer RNA for a specific codon.

60. The method according to claim 59, wherein the suppressor is a suppressor transfer tRNA for an amber codon.

61. The method according to claim 60, wherein the selection gene is a suppressor of an amber transfer RNA, and the host cell contains a gene essential under certain culture conditions comprising an amber mutation.

62. The method according to claim 50, wherein the extrachromosomal DNA molecule further comprises a target region for the site-specific recombinase.

63. The method according to claim 62, wherein the target region for the site-specific recombinase is a cer fragment from ColE1.

64. An extrachromosomal DNA molecule comprising a heterologous gene encoding a protein, a selection gene encoding a suppressor transfer RNA for a specific codon a target for a site-specific recombinase and a conditional origin of replication whose functionality in a prokaryotic host cell requires a replication initiating protein specific for said origin of replication and foreign to the prokaryotic host cell, wherein said DNA molecule does not encode the replication initiating protein.

65. The extrachromosomal DNA molecule according to claim 64, wherein the conditional origin of replication originates from a bacterial plasmid or a bacteriophage.

66. The extrachromosomal DNA molecule according to claim 65, wherein the bacterial plasmid or the bacteriophage is selected from the group consisting of RK2, R6K, R1, pSC101, Rtsl, F, RSF1010, P1, P4, lambda, Phi82 and Phi80.

67. The extrachromosomal DNA molecule according to claim 66, wherein the bacterial plasmid is R6K.

68. The extrachromosomal DNA molecule according to claim 67, wherein the conditional origin of replication comprises the gamma origin of replication of plasmid R6K.

69. The extrachromosomal DNA molecule according to claim 68, wherein the conditional origin of replication comprises SEQ ID No: 1.

70. The extrachromosomal DNA molecule according to claim 64, wherein the suppressor is a suppressor transfer tRNA for an amber codon.

71. The extrachromosomal DNA molecule according to claim 64, wherein the target region for the site-specific recombinase is a cer fragment from ColE1.

72. The extrachromosomal DNA molecule according to claim 64, wherein the heterologous gene is under the control of a bacteriophage T7 promoter.

73. A prokaryotic recombinant host cell comprising a heterologous replication initiating protein that activates a conditional origin of replication, a selection gene encoding a suppressor transfer RNA for a specific codon, and an extrachromosomal DNA molecule comprising a heterologous gene encoding a protein, a target region for a site-specific recombinase, and a conditional origin of replication whose functionality in the prokaryotic recombinant host cell requires a replication initiating protein specific for said origin of replication and foreign to the host cell, wherein said DNA molecule does not encode the replication initiating protein.

74. The prokaryotic recombinant host cell according to claim 73, wherein the cell is *Escherichia coli*.

75. The prokaryotic recombinant host cell according to claim 73, wherein the conditional origin of replication is from a bacterial plasmid or a bacteriophage.

76. The prokaryotic recombinant host cell according to claim 75, wherein the conditional origin of replication is from a bacterial plasmid or a bacteriophage selected from the group consisting of RK2, R6K, R1, pSC101, Rtsl, F, RSF1010, P1, P4, lambda, Phi82 and Phi80.

77. The prokaryotic recombinant host cell according to claim 76, wherein the conditional origin of replication is from bacterial plasmid R6K.

78. The prokaryotic recombinant host cell according to claim 73, wherein the host cell expresses a π initiator protein.

79. A prokaryotic recombinant host cell comprising a heterologous replication initiator protein encoded by gene pir-116, and an extrachromosomal DNA molecule comprising a heterologous gene encoding a protein, a target region for a site-specific recombinase, and a conditional origin of replication whose functionality in the prokaryotic recombinant host cell requires the replication initiating protein encoded by gene pir-116, wherein said DNA molecule does not comprise gene pir-116.

80. The prokaryotic recombinant host cell according to claim 79, wherein the heterologous replication initiator protein is encoded by SEQ ID No.: 2.

81. A method for producing an extrachromosomal DNA molecule comprising a heterologous gene encoding a protein, a target region for a site-specific recombinase, a selection gene encoding a suppressor transfer RNA for a specific codon, and a conditional origin of replication whose functionality in a prokaryotic host cell requires a replication initiating protein specific for said origin of replication and foreign to the host cell, wherein said DNA molecule does not encode the replication initiating, comprising:
a) culturing a prokaryotic recombinant host cell according to claim 73; and
b) isolating the extrachromosomal DNA molecule produced by the host cell.

82. The method according to claim 81, wherein the prokaryotic recombinant host cell is *Escherichia coli*.

83. The method according to claim 81, wherein the conditional origin of replication originates from a bacterial plasmid or a bacteriophage.

84. The method according to claim 83, wherein the bacterial plasmid or the bacteriophage is selected from the group consisting of RK2, R6K, R1, pSC101, Rtsl, F, RSF1010, P1, P4, lambda, Phi82 and Phi80.

85. The method according to claim 84, wherein the bacterial plasmid is R6K.

86. The method according to claim 85, wherein the conditional origin of replication comprises SEQ ID No. 1.

87. The method according to claim 81, wherein the prokaryotic recombinant host cell expresses a π initiator protein.

88. The method according to claim 81, wherein the suppressor is a suppressor transfer tRNA for an amber codon.

89. The method according to claim 88, wherein the selection gene is a suppressor transfer RNA for an amber codon, and the host cell contains a gene essential under certain culture conditions comprising an amber codon.

90. The method according to claim 81, wherein the target region for the site-specific recombinase is a cer fragment from ColE1.

91. An extrachromosomal DNA molecule comprising a heterologous gene encoding a protein, a cer fragment from ColE1, a selection gene, wherein the selection gene does not impart resistance to an antibiotic, and a conditional origin of replication whose functionality in a prokaryotic host cell requires a replication initiating protein specific for said origin of replication and foreign to the prokaryotic host cell, wherein said DNA molecule does not encode the replication initiating protein.

92. The extrachromosomal DNA molecule according to claim 91, wherein the conditional origin of replication originates from a bacterial plasmid or a bacteriophage.

93. The extrachromosomal DNA molecule according to claim 92, wherein the bacterial plasmid or the bacteriophage is selected from the group consisting of RK2, R6K, R1, pSC101, Rtsl, F, RSF1010, P1, P4, lambda, Phi82 and Phi80.

94. The extrachromosomal DNA molecule according to claim 93, wherein the bacterial plasmid is R6K.

95. The extrachromosomal DNA molecule according to claim 94, wherein the conditional origin of replication comprises the gamma origin of replication of plasmid R6K.

96. The extrachromosomal DNA molecule according to claim 95, wherein the conditional origin of replication comprises SEQ ID No: 1.

97. The extrachromosomal DNA molecule according to claim 91, wherein the selection gene encodes a suppressor transfer RNA for a specific codon.

98. The extrachromosomal DNA molecule according to claim 97, wherein the suppressor is a suppressor transfer tRNA for an amber codon.

99. The extrachromosomal DNA molecule according to claim 91, wherein the heterologous gene encodes thymidine kinase (tk).

100. The extrachromosomal DNA molecule according to claim 91, wherein the heterologous gene encodes acidic fibroblast growth factor.

101. A method for producing an extrachromosomal DNA molecule comprising a heterologous gene encoding a protein, a target region for a site-specific recombinase, and a conditional origin of replication whose functionality in a prokaryotic recombinant host cell requires a replication initiating protein encoded by gene pir-116, wherein said DNA molecule does not comprise gene pir-116, comprising:
   a) culturing a prokaryotic recombinant host cell according to claim 79; and
   b) isolating the extrachromosomal DNA molecule produced by the host cell.

102. The method of claim 101, wherein the replication initiator protein is encoded by SEQ ID No.: 2.

* * * * *

UNITED STATES PATENT AND TRADEMARK OFFICE
CERTIFICATE OF CORRECTION

PATENT NO. : 6,977,174 B2
DATED : December 20, 2005
INVENTOR(S) : J. Crouzet et al.

It is certified that error appears in the above-identified patent and that said Letters Patent is hereby corrected as shown below:

Column 33,
Lines 61-62, "to wherein" should read -- to claim 41, wherein --.

Column 35,
Lines 3-4, "codon a target for" should read -- codon, a target region for --.

Signed and Sealed this

Seventh Day of March, 2006

JON W. DUDAS
*Director of the United States Patent and Trademark Office*